(12) United States Patent
Tureci et al.

(10) Patent No.: US 7,385,044 B2
(45) Date of Patent: Jun. 10, 2008

(54) ISOLATED PEPTIDES WHICH BIND TO MHC CLASS II MOLECULES, AND USES THEREOF

(75) Inventors: Ozlem Tureci, Homburg/Saar (DE); Ugur Sahin, Homburg/Saar (DE); Michael Pfreundschuh, Homburg/Saar (DE)

(73) Assignee: Ludwig Institute for Cancer Research, New York, NY (US)

( * ) Notice: Subject to any disclaimer, the term of this patent is extended or adjusted under 35 U.S.C. 154(b) by 668 days.

(21) Appl. No.: 10/851,884

(22) Filed: May 21, 2004

(65) Prior Publication Data

US 2004/0214284 A1    Oct. 28, 2004

Related U.S. Application Data

(60) Division of application No. 09/408,036, filed on Sep. 29, 1999, now Pat. No. 6,800,730, and a continuation-in-part of application No. 09/344,040, filed on Jun. 25, 1999, now Pat. No. 6,548,064, which is a continuation-in-part of application No. 09/165,546, filed on Oct. 2, 1998, now Pat. No. 6,723,832.

(51) Int. Cl.
*C07H 21/00* (2006.01)
*C12N 15/00* (2006.01)
*C12N 5/00* (2006.01)

(52) U.S. Cl. .................... 536/23.1; 536/23.5; 435/325; 435/320.1

(58) Field of Classification Search ..................... None
See application file for complete search history.

*Primary Examiner*—Christina Chan
*Assistant Examiner*—F. Pierre VanderVegt
(74) *Attorney, Agent, or Firm*—Fulbright & Jaworski LLP

(57) ABSTRACT

Peptides which have an amino acid sequence identical to sequences found in tumor rejection antigen precursors, such as NY-ESO-1, and SSX-2, are disclosed. These peptides bind to MHC-Class II molecules, such as HLA-DR molecules, and provoke proliferation of CD4+ cells.

15 Claims, 3 Drawing Sheets

FIG. 3

```
              ATCCTCGTGGGCCCTGACCTTCTCTCTGAGAGCCGGGCAGAGGCTCCGGAGC
                      Myr      Myr     (P)
        M   Q   A   E   G   R   G   T   G   G   S   T   G   D   A   D   G   P   G   G
        CATGCAGGCCGAAGGCCGGGGCACAGGGGGTTCGACGGGCGATGCTGATGGCCCAGGAGG

P   G   I   P   D   G   P   G   G   N   A   G   G   P   G   E   A   G   A   T
        CCCTGGCATTCCTGATGGCCCAGGGGGCAATGCTGGCGGCCCAGGAGAGGCGGGTGCCAC

G   G   R   G   P   R   G   A   G   A   A   R   A   S   G   P   G   G   G   A
        GGGCGGCAGAGGTCCCCGGGGCGCAGGGGCAGCAAGGGCCTCGGGGCCGGGAGGAGGCGC

P   R   G   P   H   G   G   A   A   S   G   L   N   G   C   C   R   C   G   A
        CCCGCGGGGTCCGCATGGCGGCGCGGCTTCAGGGCTGAATGGATGCTGCAGATGCGGGGC
                                                                       (P)
        R   G   P   E   S   R   L   L   E   F   Y   L   A   M   P   F   A   T   P   M
        CAGGGGGCCGGAGAGCCGCCTGCTTGAGTTCTACCTCGCCATGCCTTTCGCGACACCCAT

E   A   E   L   A   R   R   S   L   A   Q   D   A   P   P   L   P   V   P   G
        GGAAGCAGAGCTGGCCCGCAGGAGCCTGGCCCAGGATGCCCCACCGCTTCCCGTGCCAGG
                                                        (P)                    (P)
        V   L   L   K   E   F   T   V   S   G   N   I   L   T   I   R   L   T   A   A
        GGTGCTTCTGAAGGAGTTCACTGTGTCCGGCAACATACTGACTATCCGACTGACTGCTGC

D   H   R   Q   L   Q   L   S   I   S   S   C   L   Q   Q   L   S   L   L   M
        AGACCACCGCCAACTGCAGCTCTCCATCAGCTCCTGTCTCCAGCAGCTTTCCCTGTTGAT

W   I   T   Q   C   F   L   P   V   F   L   A   Q   P   P   S   G   Q   R   R
        GTGGATCACGCAGTGCTTTCTGCCCGTGTTTTTGGCTCAGCCTCCCTCAGGGCAGAGGCG
             *
        CTAAGCCCAGCCTGGCGCCCCTTCCTAGGTCATGCCTCCTCCCCTAGGGAATGGTCCCAG
        CACGAGTGGCCAGTTCATTGTGGGGCCTGATTGTTTGTCGCTGGAGGAGGACGGCTTAC
        ATGTTTGTTTCTGTAGAAAATAAAACTGAGCTACGAAAAA
```

ISOLATED PEPTIDES WHICH BIND TO MHC CLASS II MOLECULES, AND USES THEREOF

RELATED APPLICATIONS

This application is a divisional application of Ser. No. 09/408,036 filed Sep. 29, 1999, now U.S. Pat. No. 6,800,730, which is a continuation in part of Ser. No. 09/165,546, filed on Oct. 2, 1998, now U.S. Pat. No. 6,723,832 and Ser. No. 09/344,040, filed on Jun. 25, 1999, now U.S. Pat. No. 6,548,064, all of which are incorporated herein by reference.

FIELD OF THE INVENTION

This invention relates to HLA binding peptides derived from antigens associated with cancer. These peptides bind to Class II MHC molecules.

BACKGROUND AND PRIOR ART

It is fairly well established that many pathological conditions, such as infections, cancer, autoimmune disorders, etc., are characterized by the inappropriate expression of certain molecules. These molecules thus serve as "markers" for a particular pathological or abnormal condition. Apart from their use as diagnostic "targets", i.e., materials to be identified to diagnose these abnormal conditions, the molecules serve as reagents which can be used to generate diagnostic and/or therapeutic agents. A by no means limiting example of this is the use of cancer markers to produce antibodies specific to a particular marker. Yet another non-limiting example is the use of a peptide which complexes with an MHC molecule, to generate cytolytic T cells against abnormal cells.

Preparation of such materials, of course, presupposes a source of the reagents used to generate these. Purification from cells is one laborious, far from sure method of doing so. Another preferred method is the isolation of nucleic acid molecules which encode a particular marker, followed by the use of the isolated encoding molecule to express the desired molecule.

To date, two strategies have been employed for the detection of such antigens, in e.g., human tumors. These will be referred to as the genetic approach and the biochemical approach. The genetic approach is exemplified by, e.g., dePlaen et al., Proc. Natl. Sci. USA 85: 2275 (1988), incorporated by reference. In this approach, several hundred pools of plasmids of a cDNA library obtained from a tumor are transfected into recipient cells, such as COS cells, or into antigen-negative variants of tumor cell lines which are tested for the expression of the specific antigen. The biochemical approach, exemplified by, e.g., O. Mandelboim, et al., Nature 369: 69 (1994) incorporated by reference, is based on acidic elution of peptides which have bound to MHC-class I molecules of tumor cells, followed by reversed-phase high performance liquid chromatography (HPLC). Antigenic peptides are identified after they bind to empty MHC-class I molecules of mutant cell lines, defective in antigen processing, and induce specific reactions with cytotoxic T-lymphocytes. These reactions include induction of CTL proliferation, TNF release, and lysis of target cells, measurable in an MTT assay, or a $^{51}$Cr release assay.

These two approaches to the molecular definition of antigens have the following disadvantages: first, they are enormously cumbersome, time-consuming and expensive; and second, they depend on the establishment of cytotoxic T cell lines (CTLs) with predefined specificity.

The problems inherent to the two known approaches for the identification and molecular definition of antigens is best demonstrated by the fact that both methods have, so far, succeeded in defining only very few new antigens in human tumors. See, e.g., van der Bruggen et al., Science 254: 1643-1647 (1991); Brichard et al., J. Exp. Med. 178: 489-495 (1993); Coulie, et al., J. Exp. Med. 180: 35-42 (1994); Kawakami, et al., Proc. Natl. Acad. Sci. USA 91: 3515-3519 (1994).

Further, the methodologies described rely on the availability of established, permanent cell lines of the cancer type under consideration. It is very difficult to establish cell lines from certain cancer types, as is shown by, e.g., Oettgen, et al., Immunol. Allerg. Clin. North. Am. 10: 607-637 (1990). It is also known that some epithelial cell type cancers are poorly susceptible to CTLs in vitro, precluding routine analysis. These problems have stimulated the art to develop additional methodologies for identifying cancer associated antigens.

One key methodology is described by Sahin, et al., Proc. Natl. Acad. Sci. USA 92: 11810-11913 (1995), incorporated by reference. Also, see U.S. Pat. No. 5,698,396, and patent application Ser. No. 08/479,328 filed Jan. 3, 1996. All three of these references are incorporated by reference. To summarize, the method involves the expression of cDNA libraries in a prokaryotic host. (The libraries are secured from a tumor sample). The expressed libraries are then immunoscreened with absorbed and diluted sera, in order to detect those antigens which elicit high titer humoral responses. This methodology is known as the SEREX method ("Serological identification of antigens by Recombinant Expression Cloning"). The methodology has been employed to confirm expression of previously identified tumor associated antigens, as well as to detect new ones. See the above referenced patent applications and Sahin, et al., supra, as well as Crew, et al., EMBO J 144: 2333-2340 (1995).

The SEREX methodology has been employed in a number of instances to identify cancer associated antigens. See, e.g., PCT/US99/06875, describing a cancer associated antigen found to be expressed by, inter alia, esophageal cancer and melanoma. This antigen is referred to as NY-ESO-1. See U.S. Pat. No. 5,804,381 as well as Chen, et al, Proc. Natl. Acad Sci USA—92:8125-8129 (1995). Additionally, a family of related antigens, the "SSX" family, has been identified using this methodology. See PCT/US99/14493 and Ser. No. 09/105,839 filed Jun. 26, 1998 in this regard.

Following the identification of full length molecules as cancer associated antigens, the next step has been to identify those portions of the antigens which are relevant as binding partners for MHC or HLA molecules. The resulting complexes serve as targets for identification by T cells, which then proliferate and eliminated the cells which present such complexes.

Early work focused on the identification of those peptide molecules which bind to Class I molecules stimulating proliferation of CD8$^+$ T cells. See, e.g., U.S. Pat. No. 5,925,729, which shows this for one family of antigens. Also see PCT/US99/06875 and PCT/US99/14493 for further work on the identification of peptides which bind to MHC molecules. All of these are incorporated by reference.

The presence of antibodies against a particular molecule suggests that a process other than presentation by MHC Class I molecules is involved. In PCT/US99/06875, supra, evidence is presented showing that the NY-ESO-1 molecule is processed to peptides which are presented by MHC Class II molecules.

This work has been continued. The disclosure which follows shows that additional peptides have been identified which bind to MHC Class II molecules, and stimulate proliferation of CD4+ T cells. These peptides are derived from both NY-ESO-1 and SSX-2. These, and other features of the invention, are set forth in the disclosure which follows.

BRIEF DESCRIPTION OF THE FIGURES

FIG. 3 shows potential sites for modification of the deduced amino acid sequence of NY-ESO-1.

DETAILED DESCRIPTION OF PREFERRED EMBODIMENTS

EXAMPLE 1

Figure 1A:
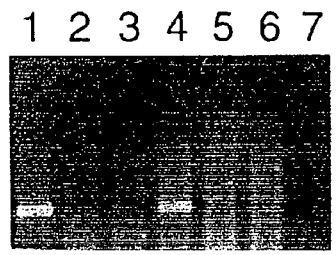
FIG. 1 shows the expression pattern of RNA for the NY-ESO-1 antigen, in various tissue types.
Figure 1B:
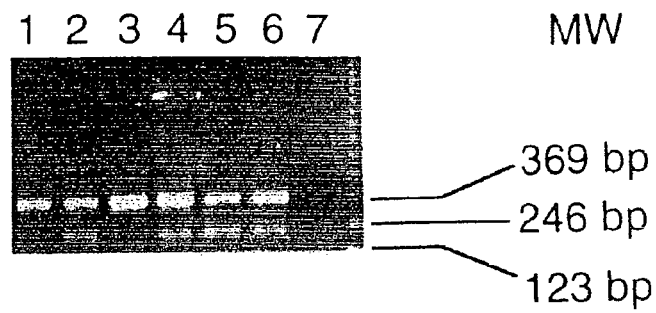
Figure 2:
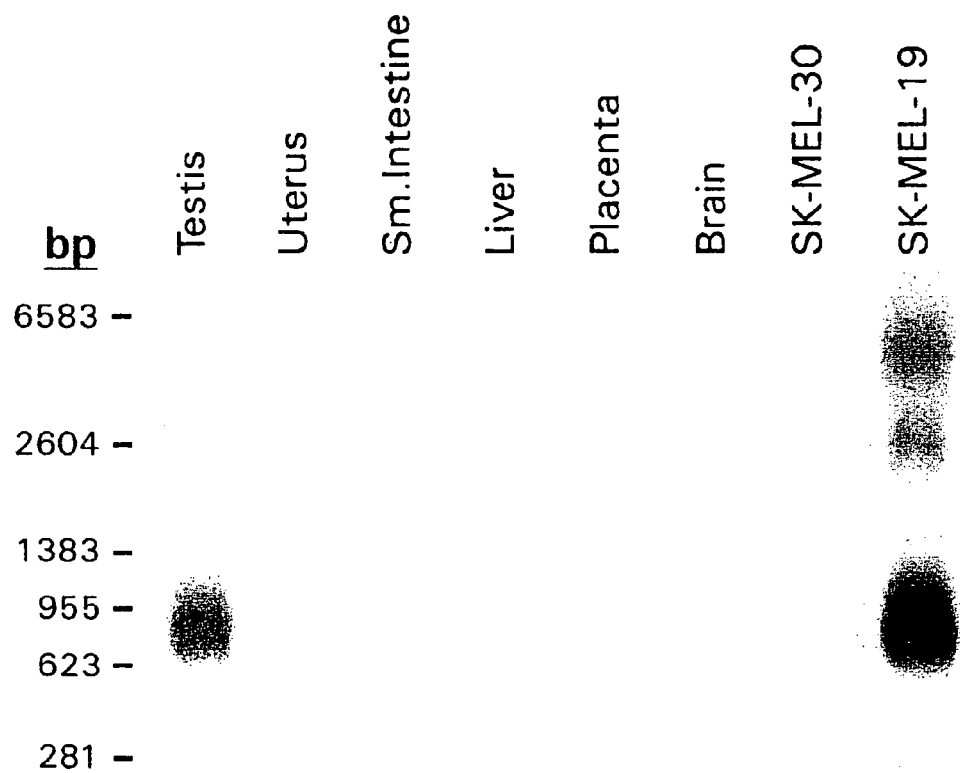
FIG. 2 shows Northern Blot analysis of NY-ESO-1 mRNA, which was found in testis and cell line SK-MEL-19, but not in various other cell and tissue samples.
Figure 4:
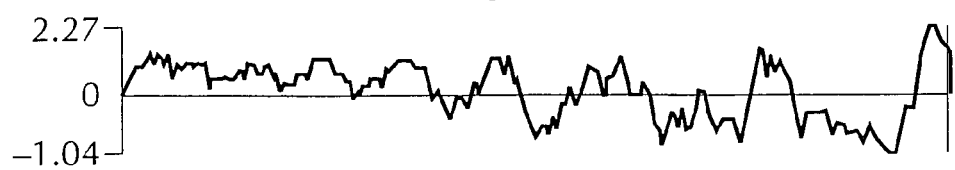
FIG. 4 is a hydrophilicity plot of NY-ESO-1, showing hydrophilic domains in the amino terminus and a long, hydrophobic stretch close to the carboxyl end.

Total RNA was extracted from a snap frozen specimen of well to moderately differentiated squamous cell cancer of the esophagus, using well known methods. See, e.g., Chomzynski, J. Analyt. Biochem. 162: 156-159 (1987), for one such method. This RNA was used to prepare a cDNA library which was then transfected into λZAP phage vectors, in accordance with the manufacturer's instructions. The λZAP library was then transfected into $E.\ coli$, yielding $1.6 \times 10^6$ primary isolates.

The SEREX methodology of Sahin, et al., Proc. Natl. Acad. Sci. USA 92: 11810-11813 (1995), incorporated by reference, was then used. In brief, autologous serum was stripped of antibodies against molecules which are endogenous to $E.\ coli$ by combining the serum with lysates of $E.\ coli$ transfected with phage λZAP which did not contain the cDNA clones from the esophageal cancer cells.

The depleted serum was then diluted, and mixed with nitrocellulose membranes containing phage plaques. The plaques were incubated overnight, at room temperature. Washing followed, and then the filters were incubated with alkaline phosphatase conjugated goat anti human FCγ secondary antibodies, and reactive phage plaques were visualized by incubating with 5-bromo-4-chloro-indolyl phosphate and nitroblue tetrazolium. A total of 13 positive clones were found.

EXAMPLE 2

Following identification, the reactive clones were subcloned to monoclonality via dilution cloning and testing with human serum. These clones were then purified, excised in vitro, and converted into pBK-CMV plasmid forms, using the manufacturer's instructions. The inserted DNA was then evaluated using EcoRI-XbaI restriction mapping to determine different inserts. Eight different inserts were identified, ranging in size from about 500 to about 1.3 kilobase pairs. The clones were sequenced using an ABI PRISM automated sequencer.

Table 1 summarizes the results. One gene was represented by four overlapping clones, a second by three overlapping clones, and the remaining six by one clone only.

A homology search revealed that the clones referred to as NY-ESO-2, 3, 6, 7 were already known. See Elisei, et al., J. Endocrin. Invest. 16: 533-540 (1993); Spritz, et al., Nucl. Acids Res. 15: 10373-10391 (1987); Rabbits, et al., Nature Genetics 4: 175-180 (1993); Crozat, et al., Nature 363: 640-644 (1993); GenBank H18368 and D25606. Two of the clones (NY-ESO-3 and NY-ESO-6), have previously been shown to be expressed in various normal human tissues. No evidence of lineage restriction has been found. NY-ESO-6 (cDNA), appears to be the 3'-untranslated portion of the FUS/TLS gene. In experiments not reported here, sequencing and Southern Blot analysis of NY-ESO-6 showed no evidence of translocation or point mutations in the cancer. Four of the clones, i.e., NY-ESO-1, 4, 5 and 8 showed no strong homology to sequences in the databases examined, and were thus studied further.

TABLE 1

Genes isolated from esophageal cancer library by immunoscreening with autologous serum

| GENE | CLONE# | Size | DNA databank | Comments |
|---|---|---|---|---|
| NY-ESO-1 | E1-5b | 679 bp | No strong homology | expressed in testis and ovary |
|  | E1-114b | 614 bp |  |  |
|  | E1-153c | 670 bp |  |  |
|  | E1-50 | 679 bp |  |  |
| NY-ESO-2 | E1-71a | 605 bp | U1 small nuclear | cloned by Ab screening (thyroiditis patient) |
|  | E1-140 | 874 bp | RNP 1 homolog |  |
|  | E1-31 | 750 bp |  |  |
| NY-ESO-3 | E1-141b | 517 bp | Colon 3' direct MboI cDNA; Adult brain cDNA | (dbj D25606, gb H18638) unpublished |
| NY-ESO-4 | E1A-10c | 400 bp | No strong homology | ubiquitous expression in normal tissues |
| NY-ESO-5 | E1A-54 | 670 bp | No strong homology | expressed in normal esophagus |
| NY-ESO-6 | E1B-9b | ~1.2 kb | Human fus mRNA | translocated in liposarcoma t(12; 16) |
| NY-ESO-7 | E1B-20f | ~1.0 kb | human U1-70k sn RNP | different from NY-ESO-2 (embl HSU17052, gbM22636) |

TABLE 1-continued

Genes isolated from esophageal cancer library by immunoscreening with autologous serum

| GENE | CLONE# | Size | DNA databank | Comments |
|---|---|---|---|---|
| NY-ESO-8 | E1B-20g | ~1.3 kb | No strong homology | ubiquitous expression in normal tissues |

EXAMPLE 3

Studies were carried out to evaluate mRNA expression of the NY-ESO 1, 4, 5 and 8 clones. To do this, specific oligonucleotide primers were designed for each sequence, such that cDNA segments of 300-400 base pairs could be amplified, and so that the primer melting temperature would be in the range of 65-70° C. Reverse transcription-PCR was then carried out using commercially available materials and standard protocols. A variety of normal and tumor cell types were tested. The clones NY-ESO-4 and NY-ESO-8 were ubiquitous, and were not studied further. NY-ESO-5 showed high level expression in the original tumor, and in normal esophageal tissue, suggesting that it was a differentiation marker.

NY-ESO-1 was found to be expressed in tumor mRNA and in testis, but not normal colon, kidney, liver or brain tissue. This pattern of expression is consistent with other tumor rejection antigen precursors.

EXAMPLE 4

The RT-PCR assay set forth supra was carried out for NY-ESO-1 over a much more complete set of normal and tumor tissues. Tables 2, 3 and 4 show these results. In brief, NY-ESO-1 was found to be highly expressed in normal testis and ovary cells. Small amounts of RT-PCR production were found in normal uterine myometrium, and not endometrium, but the positive showing was not consistent. Squamous epithelium of various cell types, including normal esophagus and skin, were also negative.

When tumors of unrelated cell lineage were tested, 2 of 11 melanomas cell lines showed strong expression, as did 16 of 67 melanoma specimens, 6 of 33 breast cancer specimens and 4 of 4 bladder cancer. There was sporadic expression in other tumor types.

TABLE 2 mRNA distribution of NY-ESO-1 in normal tissues

| Tissue | mRNA | Tissue | mRNA |
|---|---|---|---|
| Esophagus | − | Adrenal | − |
| Brain* | − | Pancreas | − |
| Fetal Brain | − | Seminal Vesicle | − |
| Heart | − | Placenta | − |
| Lung | − | Thymus | − |
| Liver | − | Lymph node | − |
| Spleen | − | Tonsil | − |
| Kidney | − | PBL | − |
| Stomach | − | PBL, activated# | − |
| Small intestine | − | Melanocytes | − |
| Colon | − | Thyroid | − |
| Rectum | − | Uterus | +/−** |
| Breast | − | Testis | + |
| Skin | − | Ovary | + |

*tissues from several parts tested with IL-2 and PHA
**weakly positive in some specimens, negative by Northern blot

TABLE 3 mRNA distribution of NY-ESO-1 in melanoma and breast cancer cell lines:

| Cell line | NY-ESO-1 mRNA |
|---|---|
| MZ2-MEL3.1 | − |
| MZ2-MEL2.2 | − |
| SK-MEL-13 | − |
| SK-MEL-19 | + |
| SK-MEL-23 | − |
| SK-MEL-29 | − |
| SK-MEL-30 | − |
| SK-MEL-31 | − |
| SK-MEL-33 | − |
| SK-MEL-37 | + |
| SK-MEL-179 | − |
| SK-BR-3 | − |
| SK-BR-5 | − |
| 734B | − |
| MDA-MB-231 | − |

TABLE 4

NY-ESO-1 mRNA expression in various human tumors by RT-PCR

| tumor type | mRNA (positive/total) | tumor type | mRNA (positive/total) |
|---|---|---|---|
| melanoma | 25/77 | ovarian cancer | 2/8 |
| breast cancer | 17/43 | thyroid cancer | 2/5 |
| prostate cancer | 4/16 | bladder cancer | 9/13 |
| colon cancer | 0/16 | Burkitt's lymphoma | 1/2 |
| glioma | 0/15 | basal cell carcinoma | 0/2 |
| gastric cancer | 0/12 | Jejomyosarcoma | 0/2 |
| lung cancer | 5/17 | other sarcomas | 0/2 |
| renal cancer | 0/10 | pancreatic cancer | 0/2 |
| lymphoma* | 0/10 | seminoma | 0/1 |
| hepatoma | 2/7 | spinal cord tumor | 0/1 |

*non-Hodgkin's, non-Burkitt's types.

A further set of experiments were carried out to ascertain if the presence of anti NY-ESO-1 antibody in cancer patient sera could be determined via an ELISA.

To elaborate, recombinant NY-ESO-1 in a solution of coating buffer (15 mM Na$_2$CO$_3$, 30 mM NaHCO$_3$, pH 9.6, 0.02% NaN$_3$), at a concentration of 1 ug/ml, was adsorbed to microwell plates (10 ul of solution per well), and then kept overnight at 4° C. The plates were washed with phosphate buffered saline, and blocked, overnight, at 4° C., with 10 ul/well of 2% bovine serum albumin/phosphate buffered saline. After washing, 10 ul/well of diluted serum in 2% bovine serum albumin was added to the wells. Following two hours of incubation at room temperature, plates were washed, and 10 ul/well of goat anti-human IgG-alkaline phosphatase conjugates were added, at a 1:1500 dilution. This solution was incubated for one hour at room temperature, followed by washing and addition of a solution of substrate for the alkaline phosphatase (10 ul/well). After 25 minutes at room temperature, the wells were read with a fluorescence plate reader. The results are presented in the following table:

| Cancer patients: | Eso 1+/total tested | % |
|---|---|---|
| melanoma | 12/127 | 9.4 |
| ovarian cancer | 4/32 | 12.5 |
| lung cancer | 1/24 | 4.0 |
| breast cancer | 2/26 | 7.7 |
| Blood donors | 0/70 | 0 |

In order to determine whether there was a relationship between expression of mRNA for NY-ESO-1 in tumors, and antibody response to the NY-ESO-1 protein, data from sixty-two melanoma patients were compared. All patients whose serum was reactive with NY-ESO-1 protein (i.e., contained antibodies to NY-ESO-1), also had NY-ESO-1 positive tumors, while no patients with NY-ESO-1 negative tumors showed antibodies to NY-ESO-1 in their serum. There was a percentage of NY-ESO-1 positive patients who lacked the antibody. Given that about 20-40% of melanomas expressed NY-ESO-1, and only patients with NY-ESO-1 positive tumors have antibody, the data suggest a high percentage of patients with NY-ESO-1 positive tumors develops antibodies against the protein, thus suggesting a broad scale assay useful in diagnosis and responsiveness to treatment.

EXAMPLE 5

Northern blot analysis was then carried out to investigate the size of the NY-ESO-1 transcript, and to confirm tissue expression patterns. The methodology of Ausubel, et al., *Current Protocols In Molecular Biology* (John Wiley & Sons, 1995) was used. To be specific, 20 ug of total RNA per lane were dissolved in a formamide and formaldehyde containing buffer, heated to 65° C., and then separated on a 1.2% agarose gel, with 3% formaldehyde, followed by transfer to nitrocellulose paper. Hybridization was then carried out using a $^{32}P$ labelled probe, followed by high stringency washing. The final wash was at 0.1×SSC, 0.1% SDS, 60° C., for 15 minutes.

RNA from testis, and a melanoma cell line (SK-MEL-19) which had been positive for NY-ESO-1 in the prior assays, showed an RNA transcript of about 0.8-0.9 kb. An esophageal carcinoma specimen showed a smear in the 0.4-0.9 kb range, reflecting partial degradation. RNA from additional tissues or cell lines tested showed no transcript.

To get cDNA encoding the full transcript, the esophageal cDNA library was rescreened, using plaque hybridization, and the original cDNA clone as the hybridization probe. When 3×10$^5$ clones were screened, six positives were found. The three longest clones were sequenced. Analysis of open reading frames showed that all three contained the entire coding region, and 5'-untranslated regions of variable size. The longest clone, 755 base pairs in length, (excluding polyA), contains a 543 base pair coding region, together with 53 untranslated bases at the 5' end and 151 untranslated base pairs at the 3'-end. See SEQ ID NO: 1 (also, FIG. 3).

The long ORF indicated that the deduced sequence of NY-ESO-1 protein is 180 amino acids. The single immunopositive clone contained a sequence encoding 173 of these. Deduced molecular mass is 17,995 daltons.

Analysis shows that there is an abundance of glycine residues in the N-terminal portion (30 of the first 80, 4 in the remaining 100). Hydrophilicity analysis indicated that there were hydrophilic antigenic sequences in the N-terminal half of the molecule, with alternating hydrophobic and hydrophilic sequences, ending with a long, C-terminal hydrophobic tail (amino acids 152-172), followed by a short hydrophilic tail. This pattern suggests a transmembrane domain. There are several potential N-myristorylation sites, 3 phosphorylation sites, and no evidence of N-glycosylation sites.

EXAMPLE 6

A melanoma cell line "NW-MEL-38" was established, in 1995, from a patient who suffered from malignant melanoma. Serum samples, peripheral blood lymphocytes, and tumor samples, were taken from the subject and frozen, until the work described herein was carried out. In anticipation of evaluating antitumor T cell response in this patient, the patient was HLA typed as HLA-A1 and HLA-A2.

To determine whether melanoma from this patient expressed NY-ESO-1, total RNA was isolated from both tumor samples and cell line NW-MEL-38, using standard techniques. Then, two micrograms of the total RNA, from each samples were subjected to cDNA synthesis, again using standard techniques.

The cDNA was then used in RT-PCR experiments, using the following primers:

```
                                            (SEQ ID NO: 1),
5'-CACACAGGAT CCATGGATGC TGCAGATGCG G'-3', and (SEQ ID NO: 3)
CACACAAAGC TTGGCTTAGC GCCTCTGCCC TG-3'
```

These primers should amplify a segment of SEQ ID NO: 1 which spans nucleotides 271 to 599.

Amplification was carried out over 35 cycles, using an annealing temperature of 60° C. The PCR products were visualized via ethidium bromide staining, on a 1.5% agarose gel.

The results indicated that both the tumor and the cell line expressed SEQ ID NO: 1. The cell line and tumor samples were used in subsequent experiments.

EXAMPLE 7

The isolated cDNA molecule, discussed supra, was then used to make recombinant protein. Specifically, the cDNA was PCR amplified, using standard techniques, and was then cloned into a commercially available plasmid vector, i.e., pQE9, which contains His tags. In work not elaborated upon herein, a second vector, pQE9K was also used. This differs from PQE9 in that kanamycin resistance is imparted by pQE9K, rather than ampicillin resistance.

The plasmid vector was transformed into *E. coli* strain XL1-Blue, and positive transformants were identified via restriction mapping and DNA sequencing. Production of recombinant protein was induced using isopropyl β-D-thiogalactoside, and the protein was purified on an $Ni^{2+}$ ion chromatography column, following well known procedures. The protein when analyzed via 15% SDS-PAGE and silver staining, was identified as a protein with a molecular weight of about 22 kilodaltons. This is consistent with the anticipated size of the protein from its sequence. Two other forms of the recombinant protein were also identified. These consisted of amino acids 10-180, and 10-121 of the amino acid sequence reported in SEQ ID NO: 1. They have molecular weights of about 14 kD and 20 kD, respectively, on SDS-PAGE, as carried out supra.

An additional set of experiments were carried out to express NY-ESO-1 in baculovirus. To elaborate, the NY- ESO-1 cDNA insert was released from the pQE9 vector, by cleavage with BamHI and HindIII. This insert was then subcloned into a commercially available baculovirus vector which had been cleaved with the same enzymes. Positive clones were determined, using standard methods, and transfected into recipient Sf9 cells. Recombinant viruses were then used to infect insect cells, using a standard medium (IPL-41), supplemented with 10% fetal calf serum. The multiplicity of infection for the work was 20. Expression of recombinant protein was determined as described supra. The recombinant protein produced in this vector carries an His-tag, so it was purified on $Ni^{2+}$ affinity columns, also as described, supra. The protein consists of amino acids 10-180, and has a molecular weight of 20 kD via SDS-PAGE.

Additional eukaryotic transfectants were then produced. To do this, the NY-ESO-1 coding sequence was isolated from the pQE9 vector described supra, and then cloned into BamHI-HindIII sites of eukaryotic expression vector pcDNA 3.1. Next, COS-7 cells were transfected with this vector, by contacting cell samples with 150 ng of the plasmid discussed supra, and 150 ng of plasmid pcDNA 1 Amp, which contained either cDNA for HLA-A2.1 or cDNA for HLA-A1, The well known DEAE-dextran chloroquine method was used. The cells were then incubated at 37° C., for 48 hours, after which they were tested in a CTL stimulation assay. Specifically, the assay followed Traversari et al, Immunogenetics 35: 145-148 (1992), incorporated by reference. In brief, 2500 CTLs, (NW38-IVS-1, see example 9, infra), in 100 ul RPMI supplemented with 100% human serum, and 25 U/ml of recombinant IL-2 were added to microwells containing COS-7 transfectants (20,000 cells/well). After 24 hours, 50 ul of supernatant were collected from each well, and TNF-α levels were determined in a standard assay, i.e., one where cytotoxicity against WEHI 164 clone 13 cells were tested, using MTT. Positive cells were used in the Western Blot analysis, described in the example which follows.

The CTLs used were CTL NW38-IVS-1, prepared in accordance with Knuth et al., Proc. Natl. Acad. Sci. USA 81: 3511-3515 (1984), incorporated by reference. Specifically, mixed lymphocyte T cell cultures were set up, by combining $10^5$ autologous NW38 MEL-1 tumor cells, and $10^6$ peripheral blood lymphocytes, taken from the subject. The cytokine IL-2 was added, and the mixed culture was incubated for one week at 37° C. Tumor cells were removed, and a new aliquot of $5 \times 10^4$ tumor cells were added together with IL-2. This process was repeated weekly, until a strong response was seen when tested against $^{51}Cr$ labelled NW-MEL-38 cells. The responder T cells were collected and frozen until used in further experiments.

EXAMPLE 8

Western Blot analysis was then carried out, using the serum samples described supra, as well as cell lysates taken from the cell line NW-MEL-38, described supra, and the COS-7 transfectants, described supra, and the purified recombinant protein, also described supra. Serum samples were taken from various points of the patient's therapy. There was no difference in the results.

In these assays, 1 ug of recombinant NY-ESO-1 protein, or 5 ul of cell lysates of either type were diluted in SDS and boiled for five minutes, and then electrophoresed on a 15% SDS gel. After overnight blotting on nitrocellulose (0.45 um), and blocking with 3% BSA, the blots were incubated with serum, diluted at 1:1000, 1:10,000, and 1:100,000, or with a monoclonal antibody against NY-ESO-1, diluted to 1:50, as a positive control. The monoclonal antibody was prepared via Chen, et al., Proc. Natl. Acad. Sci. USA 5915-5919 (1996), incorporated by reference and elaborated as follows. BALB/C mice were immunized via five subcutaneous injections of recombinant NY-ESO-1 protein, at 2-3 week intervals. The immunizing formulation included 50 ug of recombinant protein in adjuvant. The first injection used Complete Freund's Adjuvant, and Incomplete Freund's Adjuvant was used thereafter. Spleen cells were taken from the immunized mice, and fused with mouse myeloma cell line SP2/0, to generate hybridomas. Representative hybridoma E978 was used for generation of mAbs.

Once hybridomas were generated, they were cloned, and their supernatants were screened against recombinant protein, using a standard solid phase ELISA on microtiter plates. The assay was in accordance with Dippold et al., Proc. Natl. Acad. Sci. USA 77: 6114-6118 (1980), incorporated by reference. A series of negative controls were also run, using recombinant NY-ESO-1. Serum antibodies which bound to recombinant protein, produced by E. coli as described, supra were visualized using goat anti-human IgG, labelled with alkaline phosphatase at 1:10,000 dilution, and were then visualized with NBT-phosphate. Untransfected COS-7 cells were also used as a control. Serum from a healthy individual was also used as a control.

Strong reactivity against the recombinant protein was found at serum dilutions down to 1:100,000, and there was also reactivity against lysate of NW-MEL-38. There was no reactivity found against the untransfected COS-7 cells, nor did the serum from a healthy individual show reactivity.

EXAMPLE 9

Four different forms of NY-ESO-1 are described supra, i.e., the form produced by SEQ ID NO: 1 in E. coli, as well as one consisting of amino acids 10-180, one consisting of amino acids 10-121, and a form, expressed in the baculovirus vector system discussed supra which consisted of amino acids 10-180. Each form was used in ELISAs, following the above described protocols. All forms of the protein were found to be equally reactive with antibodies taken from various patients, as well as the murine monoclonal antibodies discussed, supra.

EXAMPLE 10

In the testing of the COS-7 transfectants, supra, and the assays discussed in this example, a cytolytic T cell line "NW38-IVS-1" was used. This "CTL" was generated, via in vitro stimulation of the peripheral blood lymphocytes mentioned supra, using the tumor cell line NW-MEL-38. This was done using standard techniques.

Figure 5:
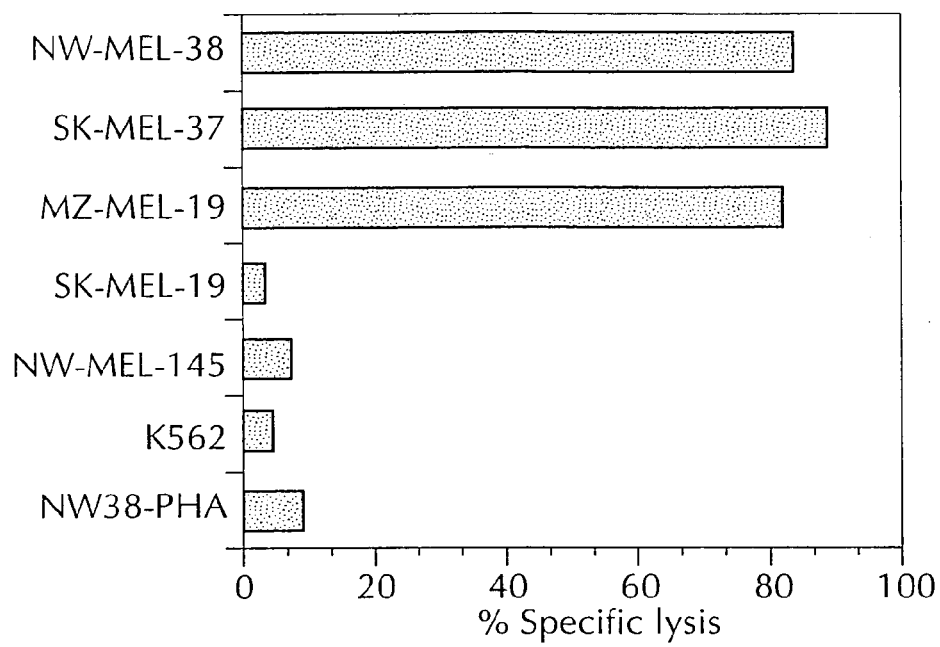
FIG. 5 shows the results of CTL lysis studies using various cells which are HLA-A2 positive, NY-ESO-1 positive, positive for both, or positive for neither.

The CTL was used in a cytotoxicity assay with NW-MEL-38 (which was HLA-A1, A2 positive, and NY-ESO-1 positive), along with two allogeneic cell lines which were NY-ESO-1 and HLA-A2 positive (SK-MEL-37 and MZ-MEL-19), a cell line which is MHC Class I negative (SK-MEL-19), a cell line which is HLA-A2 positive, but NY-ESO-1 negative (NW-MEL-145), along with control cell lines K562 and autologous phytohemagglutinin stimulated blasts. Various effector/target ratios were used, and lysis of $^{51}Cr$ labelled target cells was the parameter measured. FIG. 5 shows this.

Figure 6:
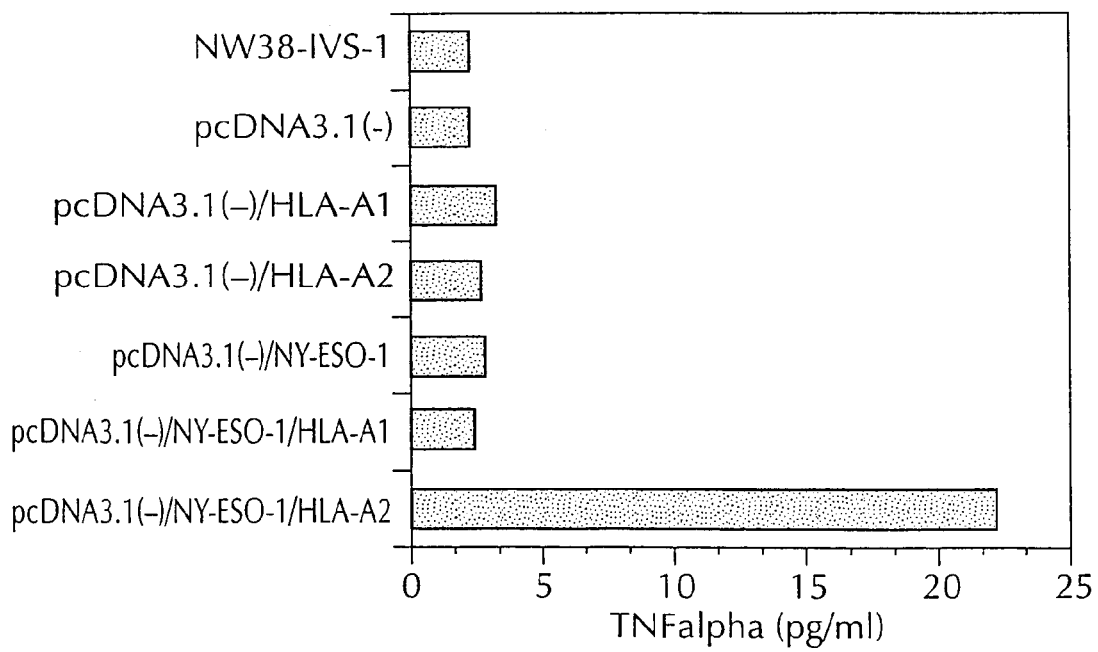
FIG. 6 presents data establishing that HLA-A2 is the presenting molecule for presentation of SEQ ID NO: 1 derived peptides.

The results indicated that the CTL NW38-IVS-1 lysed both the autologous cell line NW MEL-38, and the allogeneic cell lines which were HLA-A2 and ESO-1 positive. Hence, the CTL was reactive with allogeneic materials. See FIG. 6.

EXAMPLE 11

As patient NW38 was HLA-A1 and HLA-A2 positive, experiments were carried out to determine which MHC molecule was the presenting molecule.

The same experiment, described supra with COS-7 cells was carried out, except that, in these experiments, care was taken to secure separate groups of cotransformants which had been transformed with either HLA-A1 cDNA, or HLA-A2 cDNA, but not both. These results show that the CTL NW38-IVS-1 lysed COS-7 transfectants containing both NY-ESO-1 and HLA-A2 exclusively. See FIG. 6. The work also confirmed the specificity of the CTL, since the NY-ESO-1 negative, HLA-A2 positive cells described in Example 9 were positive for other molecules known to be processed to peptides presented by HLA-A2 molecules.

EXAMPLE 12

Once the presenting MHC molecule was identified as HLA-A2, a screening of the amino acid sequence for NY-ESO-1 was carried out, to identify all peptides which satisfy this motif, using the model set forth by D'Amaro et al., Human Immunol. 43: 13-18 (1995), and Drijfhout, et al., Human Immunol. 43: 1-12 (1995) incorporated by reference. Peptides corresponding to all of the amino acid sequences deduced thereby were synthesized, using standard techniques, and were then used in cytotoxicity assays, following Knuth et al., Proc. Natl. Acad. Sci. USA 81: 3511-3515 (1984), incorporated by reference. Specifically, cell line CEMX721.174.T2 ("T2" hereafter), was used, because it does not process antigens to MHC complexed peptides, thereby making it ideal for experiments of the type described herein. Samples of T2 cells were labelled with 100 uCi of Na($^{51}$Cr)O$_4$, using standard methods, and were then washed three times, followed by incubation with 10 ug/ml peptide and 2.5 ug/ml of β2-microglobulin. Incubation was for one hour, at room temperature. Then responder cells (100 ul of a suspension of CTL NW38-IVS-1) were added, at an effector/target ratio of 90:1, and incubated for four hours in a water saturated atmosphere, with 5% CO$_2$, at 37° C. Then, plates were centrifuged at 200×g for five minutes, 100 ul of supernatant was removed, and radioactivity was measured. The percentage of $^{51}$Cr release was determined in accordance with known strategies. it was found that the peptides SLLM-WITQCFL (SEQ ID NO: 4), SLLMWITQC (SEQ ID NO: 5), and QLSLLMWIT (SEQ ID NO: 6), were the three best stimulators of CTLs. Comparable results were found when NW-MEL-38 and cell lines SK-MEL-37 and MZ-MEL-19 were used as targets, as is shown, supra.

EXAMPLE 13

Studies were carried out to determine if CD4+ helper T cells recognized complexes of MHC-Class II molecules and peptides derived from NY-ESO-1.

Tumor cell line MZ-MEL-19 has been typed as being HLA-DR53 positive. Hence, NY-ESO-1 was screened using Futaki, et al., Immunogenetics 42:299-301 (1995), incorporated by reference, which teaches binding motifs for HLA-DR53. A total of twenty eight peptides which, in theory, would bind to HLA-DR53, and antigens presenting cells alone.

Peripheral blood lymphocytes ("PBLs"), were isolated from two patients with metastatic melanoma, who had been typed as HLA-DR53 positive.

The typing was performed using standard, commercially available reagents. One patient was typed as being positive for HLA-DRB1 (alleles 1501-05, 1601-1603, 1605 and 0701), HLA DRB4* (alleles (0101-0103), and DRB5* (alleles 0101), while the second patient was typed as positive for HLA-DRB1* (alleles 1401, 1407, 1408, and 0901), HLA-DRB3* (alleles 0201-0203), and DRB4* (alleles 0101-0103). All alleles of HLA-DRB4* are referred to as HLA-DR53, in accordance with Bodmer, et al., Human Immunol 34:4-18 (1992), incorporated by reference.

The PBLs were treated with magnetic beads coated with appropriate antibodies to deplete CD4+ and CD8+ T lymphocytes. The remaining cells were seeded in 24 well plates, at 4×10$^6$ cells/well, and were allowed to adhere to the plastic of the wells for 24 hours. Any non-adhering cells were removed, and the remaining cells were used as antigen presenting cells. These cells were stimulated with GM-CSF (1000 U/ml), and IL-4 (1000 U/ml) for 5 days, in 96-well, flat bottom nitrocellulose plates, which had been coated, overnight, at 4° C., with 5 ug/ml of anti-gamma interferon antibodies. Cells were seeded at 3.5×10$^5$ cells/well.

The cells were then pulsed with 4 ug/well of test peptide, or 2 ug/well of the complete NY-ESO-1 protein, as a control.

Then CD4+ T cells were added (1×10$^5$) cells/well, in RPMI 1640 medium augmented with 10% human serum, L-asparagine (50 mg/l), L-arginine (242 mg/l), and L-glutamine (300 mg/l), together with 2.5 ng/ml of IL-2, to a final volume of 100 ul).

This mixture was incubated for 48 hours at 37° C. in a water saturated atmosphere. Then, plates were washed, 6 times, with a solution of 0.05% Tween 20/PBS, and then biotinylated anti-interferon gamma antibody, was added at 0.5 ug/ml. The antibody was incubated for 2 hours at 37° C., after which plates were developed with standard reagents, for 1 hour. Substrate 3-ethyl-9-amino carbazole was added, and incubated for 5 minutes, with positives being represented by red spots. The number of red spots/well was indicative of the frequency of CD4+ T lymphocytes which recognized complexes of peptide and HLA-DR53, or HLA-DR53 and a peptide processed from recombinant NY-ESO-1. As controls, assays were run using reagents alone (i.e., CD4+ cells alone, and the stain alone.

The following peptides were found to sensitize the CD4+ T lymphocytes to release gamma interferon.

```
AADHRQLQLSISSCLQQL      (SEQ ID NOS.: 7-9)

VLLKEFTVSGNILTIRLT

PLPVPGVLLKEFTVSGNI
```

These three peptides satisfy the motif for binding to HLA-DR53 set forth by Futaki, et al., supra, which is an anchor residue of Tyr, Phe, Trp, or Leu, followed by Ala or Ser three residues downstream.

Additional peptides were found which bind to HLA-DR53. These peptides are:

```
GAASGLNGCCRCGARGPE      (SEQ ID NOS.: 10-12).

SRLLEFYLAMPFATPMEA

TVSGNILTIRLTAADHRQ.
```

EXAMPLE 14

A human testicular cDNA expression library was obtained, and screened, with serum from a melanoma patient identified as MZ2. See e.g., parent application U.S. Pat. No. 5,804,381 incorporated by reference; also see U.S. Pat. No. 5,698,396 also incorporated by reference; Sahin, et al., Proc. Natl. Acad. Sci. USA 92:11810-11813 (1995). This serum had been treated using the methodology described in these references. Briefly, serum was diluted 1:10, and then preabsorbed with transfected E. coli lysate. Following this preabsorption step, the absorbed serum was diluted 1:10, for a final dilution of 1:100. Following the final dilution the samples were incubated overnight at room temperature, with nitrocellulose membranes containing phage plaques prepared using the methodology referred to supra. The nitrocellulose membranes were washed, incubated with alkaline phosphatase conjugated goat anti-human $Fc_\gamma$ secondary antibodies, and the reaction was observed with the substrates 5-bromo-4-chloro-3-indolyl phosphate and nitroblue tetrazolium. In a secondary screen, any phagemids which encoded human immunoglobulin were eliminated.

A total of $3.6 \times 10^5$ pfus were screened, resulting in eight positive clones. Standard sequencing reactions were carried out, and the sequences were compared to sequence banks of known sequences.

Of the eight clones, two were found to code for known autoimmune disease associated molecules, i.e., Golgin—95 (Fritzler, et al., J. Exp. Med. 178:49-62 (1993)), and human upstream binding factor (Chan, et al., J. Exp. Med. 174:1239-1244 (1991)). Three other clones were found to encode for proteins which are widely expressed in human tissue, i.e., ribosomal receptor, collagen type VI globular domain, and rapamycin binding protein. Of the remaining three sequences, one was found to be non-homologous to any known sequence, but was expressed ubiquitously in human tissues (this was found via RT-PCR analysis, but details are not provided herein). The remaining two were found to be identical to full length HOM-MEL-40, described in Ser. No. 08/479,328, while the eighth clone was found to be almost identical to "SSX3," as described by DeLeeuw, et al., Cytogenet. Cell Genet 73:179-183 (1996), differing therefrom in only two base pair differences in the coding region. These differences are probably artifactual in nature; however, the clone also included a 43 base pair 3'-untranslated region.

EXAMPLE 15

In order to carry out Southern blotting experiments, described infra, the SSX genes were amplified, using RT-PCR.

To do this, two primers were prepared using the published SSX2 sequence i.e., MEL-40A:

See Crew, et al., EMBO J 14:2333-2340 (1995). Amplification was then carried out using 0.25 U Taq polymerase in a 25 µl reaction volume, using an annealing temperature of 60° C. A total of 35 cycles were carried out.

EXAMPLE 16

The RT-PCR methodology described supra was carried out on testicular total RNA, and the amplification product was used in southern blotting experiments.

Genomic DNA was extracted from non-neoplastic tissue samples, and then subjected to restriction enzyme digestion, using BamHI, Eco RI, or HindIII in separate experiments and then separated on a 0.7% agarose gel, followed by blotting on to nitrocellulose filters. The amplification products described supra were labeled with $^{32}$P, using well-known methods, and the labeled materials were then used as probes under high stringency conditions (65° C., aqueous buffer), followed by high stringency washes, ending with a final wash at 0.2×SSC, 0.2% SDS, 65° C.

The Southern blotting revealed more than 10 bands, in each case (i.e., each of the BamHI, EcoRI, and HindIII digests), strongly suggesting that there is a family of SSX genes which contained more than the three identified previously. In view of this observation, an approach was designed which combined both PCR cloning, and restriction map analysis, to identify other SSX genes.

EXAMPLE 17

When the sequences of SSX1, 2 and 3 were compared, it was found that they shared highly conserved 5' and 3' regions, which explained why the oligonucleotides of SEQ ID NOS: 15 and 16 were capable of amplifying all three sequences under the recited conditions, and suggested that this homology was shared by the family of SSX genes, whatever its size. Hence, the oligonucleotides of SEQ ID NOS: 3 and 4 would be sufficient to amplify the other members of the SSX gene family.

An analysis of the sequences of SSX1, 2 and 3 revealed that SSX1 and 2 contained a BglII site which was not shared by SSX3. Similarly, SSX3 contained an EcoRV site not shared by the other genes.

In view of this information, testicular cDNA was amplified, using SEQ ID NOS: 15 and 16, as described supra, and was then subjected to BglII digestion. Any BglII resistant sequences were then cloned, sequenced, and compared with the known sequences.

This resulted in the identification of two previously unidentified sequences, referred to hereafter as SSX4 and SSX5. A search of the GenBank database found two clones, identified by Accession Number N24445 and W00507, both of which consisted of a sequence—tag—derived cDNA segment. The clone identified by N24445 contained the 3'-untranslated region of SSX4, and part of its coding sequence,

```
5' - CACACAGGAT CCATGAACGG AGA,         (SEQ ID NO: 13),
``` and

```
MEL-40B:

5' - CACACAAAGC TTTGAGGGGA GTTACTCGTC ATC    (SEQ. ID NO: 14)
``` while the one identified as W00507 contained a shorter fragment of the 3'-untranslated region of SSX4, and a longer part of the coding sequence. Specifically, N24445 consists of base 344 of SSX4, through the 3-end, plus 319 bases 3' of the stop codon. The W00507 sequence consists of a 99 base pair sequence, showing no homology to SSX genes followed by a region identical to nucleotides 280 through the end of SSX4 through 67 bases 3' of the stop codon of the molecule.

Two forms of SSX4 were identified. One of these lacked nucleotides 331 to 466 but was otherwise identical to SSX4 as described supra. Further, the shorter form is an alternatively spliced variant.

In Table 1, which follows, the nucleotide and amino acid sequences of the 5 known members of the SSX family are compared. One reads the table horizontally for nucleotide homology, and vertically for amino acid homology.

TABLE 1

Nucleotide and amino acid homology among SSX family members

Nucleotide Sequence Homology (%)

| | SSX1 | SSX2 | SSX3 | SSX4 | SSX5 |
|---|---|---|---|---|---|
| SSX1 | | 89.1 | 89.6 | 89.4 | 88.7 |
| SSX2 | 78.2 | | 95.1 | 91.5 | 92.9 |
| SSX3 | 77.7 | 91.0 | | 91.1 | 92.7 |
| SSX4 | 79.3 | 79.8 | 80.9 | | 89.8 |
| SSX5 | 76.6 | 83.5 | 84.0 | 77.7 | |

Amino Acid Sequence Homology (%)

Hence, SSX1 and SSX4 share 89.4% homology on the nucleotide level, and 79.3% homology on the amino acid level.

When the truncated form of SSX4 is analyzed, it has an amino acid sequence completely different from others, due to alternate splicing and shifting of a downstream open reading frame. The putative protein is 153 amino acids long, and the 42 carboxy terminal amino acids show no homology to the other SSX proteins.

EXAMPLE 18

The genomic organization of the SSX2 genes was then studied. To do this, a genomic human placental library (in lambda phage) was screened, using the same protocol and probes described supra in the discussion of the southern blotting work. Any positive primary clones were purified, via two additional rounds of cloning.

Multiple positive clones were isolated, one of which was partially sequenced, and identified as the genomic clone of SSX2. A series of experiments carrying out standard subcloning and sequencing work followed, so as to define the exon—intron boundaries.

The analysis revealed that the SSX2, gene contains six exons, and spans at least 8 kilobases. All defined boundaries were found to observe the consensus sequence of exon/intron junctions, i.e. GT/AG.

The alternate splice variant of SSX4, discussed supra, was found to lack the fifth exon in the coding region. This was ascertained by comparing it to the SSX2 genomic clone, and drawing correlations therefrom.

EXAMPLE 19

The expression of individual SSX genes in normal and tumor tissues was then examined. This required the construction of specific primers, based upon the known sequences, and these follow, as SEQ ID NOS: 15-24.

TABLE 2

Gene-specific PCR primer sequences for individual SSX genes

| SSX 1A (5'): | 5'-CTAAAGCATCAGAGAAGAGAAGC | [nt.44-66] |
| SSX 1B (3'): | 5'-AGATCTCTTATTAATCTTCTCAGAAA | [nt.440-65] |
| SSX 2A (5'): | 5'-GTGCTCAAATACCAGAGAAGATC | [nt.41-63] |
| SSX 2B (3'): | 5'-TTTTGGGTCCAGATCTCTCGTG | [nt.102-25] |
| SSX 3A (5'): | 5'-GGAAGAGTGGGAAAAGATGAAAGT | [nt.454-75] |
| SSX 3B (3'): | 5'-CCCCTTTTGGGTCCAGATATCA | [nt.458-79] |
| SSX 4A (5'): | 5'-AAATCGTCTATGTGTATATGAAGCT | [nt.133-58] |
| SSX 4B (3'): | 5'-GGGTCGCTGATCTCTTCATAAAC | [nt.526-48 |
| SSX 5A (5'): | 5'-GTTCTCAAATACCACAGAAGATG | [nt.39-63] |
| SSX 5B (3'): | 5'-CTCTGCTGGCTTCTCGGGCCG | [nt.335-54] |

The specificity of the clones was confirmed by amplifying the previously identified cDNA for SSX1 through SSX5. Taq polymerase was used, at 60° C. for SSX1 and 4, and 65° C. for SSX2, 3 and 5. Each set of primer pairs was found to be specific, except that the SSX2 primers were found to amplify minute (less than 1/20 of SSX2) amounts of SSX3 plasmid DNA.

Once the specificity was confirmed, the primers were used to analyze testicular mRNA, using the RT-PCR protocols set forth supra.

The expected PCR products were found in all 5 cases, and amplification with the SSX4 pair did result in two amplification products, which is consistent with alternative splice variants.

The expression of SSX genes in cultured melanocytes was then studied. RT-PCR was carried out, using the protocols set forth supra. No PCR product was found. Reamplification resulted in a small amount of SSX4 product, including both alternate forms, indicating that SSX4 expression in cultured melanocytes is inconsistent and is at very low levels when it occurs.

This analysis was then extended to a panel of twelve melanoma cell lines. These results are set forth in the following table.

TABLE 3

SSX expression in melanoma cell lines detected by RT-PCR*

|  | SSX1 | SSX2 | SSX3 | SSX4 | SSX5 |
|---|---|---|---|---|---|
| MZ2-Mel 2.2 | + | + | − | − | − |
| MZ2-Mel 3.1 | + | + | − | − | − |
| SK-MEL-13 | − | − | − | − | − |
| SK-MEL-19 | − | − | − | − | − |
| SK-MEL-23 | − | − | − | − | − |
| SK-MEL-29 | − | − | − | − | − |
| SK-MEL-30 | −* | −* | − | −* | − |
| SK-MEL-31 | − | − | − | − | − |
| SK-MEL-33 | − | − | − | − | − |
| SK-MEL-37 | + | + | − | + | + |
| SK-MEL-179 | − | − | − | − | − |
| M24-MET | − | − | − | − | − |

*Positive (+) denotes strong expression. Weak positivity was observed inconsistently in SK-MEL-30 for SSX 1, 2, and 4, likely representing low level expression.

EXAMPLE 20

Additional experiments were carried out to analyze expression of the members of the SSX family in various tumors. To do this, total cellular RNA was extracted from frozen tissue specimens using guanidium isothiocyanate for denaturation followed by acidic phenol extraction and isopropanol precipitation, as described by Chomczynski, et al, Ann. Biochem 162: 156-159 (1987), incorporated by reference. Samples of total RNA (4 ug) were primed with oligodT (18) primers, and reverse transcribed, following standard methodologies. The integrity of the cDNA thus obtained was tested via amplifying B-acin transcripts in a 25 cycle, standard PCR, as described by Tureci, et al, Canc. Res. 56: 4766-4772 (1996).

In order to carry out PCR analyses, the primers listed as SEQ ID NOS: 15-24, supra were used, as well as SEQ ID NOS: 25-26, i.e.:

```
ACAGCATTAC     CAAGGACAGC     AGCCACC
GCCAACAGCA     AGATGCATAC     CAGGGAC
```

These two sequences were each used with both SEQ ID NOS: 58 and 18 in order to detect the SYT/SSX fusion transcript reported for synovial sarcoma by Clark et al, supra, and Crew, et al, supra. The amplification was carried out by amplifying 1 μl of first strand cDNA with 10 pMol of each dNTP, and 1.67 mN MgCl$_2$ in a 30 μl reaction. Following 12 minutes at 94° C. to activate the enzyme, 35 cycles of PCR were performed. Each cycle consisted of 1 minute for annealing (56° C. for SEQ ID NOS: 15 and 16; 67° C. for SEQ ID NOS: 17 and 19; 65° C. for SEQ ID NOS: 19 and 20; 60° C. for SEQ ID NOS: 21 and 22; 66° C. for SEQ ID NOS: 23 and 24; 60° C. for SEQ ID NOS: 25 and 26 and 26 and 18), followed by 2 minutes at 72° C., 1 minute at 94° C., and a final elongation step at 72° C. for 8 minutes. A 15 μl aliquot of each reaction was size fractionated on a 2% agarose gel, visualized with ethidium bromide staining, and assessed for expected size. The expected sizes were 421 base pairs for SEQ ID NOS: 15 and 16; 435 base pairs for SEQ ID NOS: 17 and 19; 381 base pairs for SEQ ID NOS 19 and 20; 413 base pairs for SEQ ID NOS: 21 and 22, and 324 base pairs for SEQ ID NOS: 23 and 24. The conditions chosen were stringent, so as to prevent cross anneling of primers to other members of the SSX family. Additional steps were also taken to ensure that the RT-PCR products were derived from cDNA, and not contaminating DNA. Each experiment was done in triplicate. A total of 325 tumor specimens were analyzed. The results are presented in Tables 4 & 5 which follow.

It is to be noted that while most of the SSX positive tumors expressed only one member of the SSX family, several tumor types showed coexpression of two or more genes.

Expression of SSX genes in synovial sarcoma was analyzed, because the literature reports that all synovial sarcoma cases analyzed have been shown to carry either the SYT/SSX1 or SYT/SSX2 translocation, at breakpoints flanked by the primer sets discussed herein, i.e., SEQ ID NO: 25/SEQ ID NO: 16; SEQ ID NO: 27/SEQ ID NO: 20; SEQ ID NO. 25/SEQ ID NO: 16; SEQ ID NO: 28/SEQ ID NO: 18. The PCR work described supra showed that SYT/SSX1 translocations were found in three of the synovial sarcoma samples tested, while SYT/SSX2 was found in one. The one in which it was found was also one in which SYT/SSX1 was found. Expression of SSX appeared to be independent of translocation.

TABLE 4

Expression of SSX genes by human neoplasms

| Tumor entity | Tissues tested | SSX1 | SSX2 | SSX3 | SSX4 | SSX5 | at lease one positive | % |
|---|---|---|---|---|---|---|---|---|
| Lymphoma | 11 | — | 4 | — | — | — | 4 | 36 |
| Breast cancer | 67 | 5 | 5 | — | 10 | — | 16 | 23 |
| Endometrial cancer | 8 | 1 | 2 | — | 1 | 1 | 1 | 13 |
| Colorectal cancer | 58 | 3 | 7 | — | 9 | 1 | 16 | 27 |
| Ovarian cancer | 12 | — | — | — | 6 | — | 6 | 50 |
| Renal cell cancer | 22 | — | 1 | — | — | — | 1 | 4 |
| Malignant melanoma | 37 | 10 | 13 | — | 10 | 2 | 16 | 43 |
| Glioma | 31 | — | 2 | — | 3 | — | 5 | 16 |
| Lung cancer | 24 | 1 | 4 | — | 1 | 1 | 5 | 21 |
| Stomach cancer | 3 | — | — | — | 1 | — | 1 | 33 |
| Prostatic cancer | 5 | — | 2 | — | — | — | 2 | 40 |
| Bladder cancer | 9 | 2 | 4 | — | 2 | — | 5 | 55 |
| Head-Neck cancer | 14 | 3 | 5 | — | 4 | 1 | 8 | 57 |
| Synovial sarcoma | 4 | — | 2 | — | 1 | 1 | 3 | 75 |
| Leukemia | 23 | — | — | — | — | — | 0 | 0 |
| Leiomyosarcoma | 6 | — | — | — | — | — | 0 | 0 |

TABLE 4-continued

Expression of SSX genes by human neoplasms

| Tumor entity | Tissues tested | SSX1 | SSX2 | SSX3 | SSX4 | SSX5 | at lease one positive | % |
|---|---|---|---|---|---|---|---|---|
| Thyroid cancer | 4 | — | — | — | — | — | 0 | 0 |
| Seminoma | 2 | — | — | — | — | — | 0 | 0 |
| Total | 325 | 25 | 50 | 0 | 48 | 7 | 89 | |

TABLE 5

Expression pattern of individual SSX genes in SSX-positive tumor samples.[1]

| | SSX1 | SSX2 | SSX4 | SSX5 |
|---|---|---|---|---|
| Breast Cancer (67 specimens) | | | | |
| 51 specimens | − | − | − | − |
| 7 specimens | − | − | + | − |
| 4 specimens | − | + | − | − |
| 2 specimens | + | − | − | − |
| 2 specimens | + | − | + | − |
| 1 specimen | + | + | + | − |
| Melanoma (37 specimens) | | | | |
| 21 specimens | − | − | − | − |
| 5 specimens | + | + | + | − |
| 4 specimens | − | + | − | − |
| 2 specimens | − | + | + | − |
| 1 specimen | + | − | − | − |
| 1 specimen | + | + | − | − |
| 1 specimen | + | − | + | − |
| 1 specimen | + | − | + | + |
| 1 specimen | + | + | + | + |
| Endomet. Cancer (8 specimens) | | | | |
| 7 specimens | − | − | − | − |
| 1 specimen | + | + | + | + |
| Glioma (31 specimens) | | | | |
| 25 specimens | − | − | − | − |
| 3 specimens | − | + | − | − |
| 2 specimens | − | − | + | − |
| Lung Cancer (24 specimens) | | | | |
| 19 specimens | − | − | − | − |
| 3 specimens | − | + | − | − |
| 1 specimen | − | − | − | + |
| 1 specimen | + | + | + | − |
| Colorectal Cancer (58 specimens) | | | | |
| 42 specimens | − | − | − | − |
| 7 specimens | − | + | − | − |
| 5 specimens | − | − | + | − |
| 3 specimens | + | − | + | − |
| 1 specimen | − | − | + | + |
| Bladder Cancer (9 specimens) | | | | |
| 4 specimens | − | − | − | − |
| 2 specimens | − | + | − | − |
| 1 specimen | − | − | + | − |
| 1 specimen | + | + | − | − |
| 1 specimen | + | + | + | − |
| Head-Neck Cancer (14 specimens) | | | | |
| 6 specimens | − | − | − | − |
| 2 specimens | + | − | − | − |

TABLE 5-continued

Expression pattern of individual SSX genes in
SSX-positive tumor samples.[1]

| 2 specimens | − | + | + | − |
| 1 specimen | − | + | − | − |
| 1 specimen | − | − | + | − |
| 1 specimen | + | + | − | − |
| 1 specimen | − | + | + | + |

| Synovial Sarcoma (4 specimens) | SSX1 | SSX2 | SSX4 | SSX5 | SYT/SSX1 | SYT/SSX5 |
|---|---|---|---|---|---|---|
| Sy1 | − | − | + | − | + | − |
| Sy2 | − | + | − | + | + | − |
| Sy3 | − | − | − | − | − | + |
| Sy4 | − | + | − | − | + | − |

EXAMPLE 21

This example details further experiments designed to identify additional peptides which bind to HLA-A2 molecules, and which stimulate CTL proliferation.

First, peripheral blood mononuclear cells ("PBMCs" hereafter) were isolated from the blood of healthy HLA-A*0201+ donors, using standard Ficoll-Hypaque methods. These PBMCs were then treated to separate adherent monocytes from non-adherent peripheral blood lymphocytes ("PBLs"), by incubating the cells for 1-2 hours, at 37° C., on plastic surfaces. Any non-adherent PBLs were cryopreserved until needed in further experiments. The adherent cells were stimulated to differentiate into dendritic cells by incubating them in AIMV medium supplemented with 1000 U/ml of IL-4, and 1000 U/ml of GM-CSF. The cells were incubated for 5 days.

Seven days after incubation began, samples of the dendritic cells ($8 \times 10^5$) were loaded with 50 µg/ml of exogenously added peptide. (Details of the peptides are provided infra). Loading continued for 2 hours, at 37° C., in a medium which contained 1000 U/ml of TNF-α, and 10,000 U/ml IL-1β. The peptide pulsed dendritic cells were then washed, twice, in excess, peptide free medium. Autologous PBLs, obtained as described, supra, were thawed, and $4 \times 10^7$ PBLs were then combined with $8 \times 10^5$ peptide leaded dendritic cells, (ratio: 50:1), in a medium which contained 5 ng/ml of IL-7 and 20 U/ml of IL-2. The cultures were then incubated at 37° C.

Lymphocyte cultures were restimulated at 14, 21, and 28 days, in the same manner as the experiment carried out after 7 days. Cytotoxicity assays were carried out, at 14, 21, and 28 days, using a europium release assay, as described by Blomberg, et al., J. Immunol. Meth. 114: 191-195 (1988), incorporated by reference, or the commercially available ELISPOT assay, which measures IFN-γ release.

The peptides which were tested were all derived from the amino acid sequence of NY-ESO-1 as is described in U.S. Pat. No. 5,804,381, to Chen, et al., incorporated by reference, or the amino acid sequences of SSX-4. The peptides tested were:

```
RLLEFYLAM          (SEQ ID NO: 27)

and

SLAQDAPPL          (SEQ ID NO: 28)
``` both of which are derived from NY-ESO-1, and
  STLEKINKT (SEQ ID NO: 29)
derived from SSX-4. The two NY-ESO-1 derived peptides were tested in ELISPOT assays. The results follow. In summary, three experiments were carried out. The results are presented in terms of the number of spots (positives) secured when the HLA-A2 positive cells were pulsed with the peptide minus the number of spots obtained using non-pulsed cells. As indicated, measurements were taken at 14, 21 and 28 days.

The following results are for peptide RLLEFYLAM.

| | Day Measured (Pulsed Cells - Unpulsed Cells) | | |
|---|---|---|---|
| | 14 | 21 | 28 |
| Expt 1 | 30 | 8 | * |
| Expt 2 | 22 | * | 12 |
| Expt 3 | 6 | * | 12 |

*not determined

EXAMPLE 22

In follow up experiments, the T cell cultures described supra were tested on both COS cells which had been transfected with HLA-A*0201 encoding cDNA and were pulsed with endogenous peptide, as described supra, or COS cells which had been transfected with both HLA-A*0201 and NY-ESO-1 encoding sequences. Again, the ELISPOT assay was used, for both types of COS transfectants. Six different cultures of T cells were tested, in two experiments per culture.

| | | Pulsed with Peptide | Endogenous NY-ESO-1 Production |
|---|---|---|---|
| Culture 1 | Expt 1 | 64 | 44 |
| | Expt 2 | 44 | 52 |
| Culture 2 | Expt 1 | 48 | 45 |
| | Expt 2 | 100 | 64 |
| Culture 3 | Expt 1 | 20 | 37 |
| | Expt 2 | 16 | 16 |
| Culture 4 | Expt 1 | 17 | 40 |
| | Expt 2 | 28 | 34 |
| Culture 5 | Expt 1 | 36 | 26 |
| | Expt 2 | 4 | 36 |
| Culture 6 | Expt 1 | 12 | 62 |
| | Expt 2 | 44 | 96 |

The fact that the endogenous NY-ESO-1 led to lysis suggests that NY-ESO-1 is processed to this peptide via HLA-A2 positive cells.

Similar experiments were carried out with the second NY-ESO-1 derived peptide, i.e., SLAQDAPPL SEQ ID NO: 28. These results follow:

|  |  | Pulsed with Peptide | Endogenous NY-ESO-1 Production |
|---|---|---|---|
| Culture 1 | Expt 1 | 28 | 16 |
|  | Expt 2 | 30 | 14 |
| Culture 2 | Expt 1 | 31 | 75 |
|  | Expt 2 | 30 | 70 |
| Culture 3 | Expt 1 | 32 | 44 |

EXAMPLE 23

In further experiments, the specificity of the CTLs generated in the prior experiment was tested by combining these CTLs with COS cells, transfected with HLA-A*0201 encoding sequences, which were then pulsed with peptide. First, the peptide RLLEFYLAM (SEQ ID NO: 27) was tested, in three experiments, and then SLAQDAPPL (SEQ ID NO: 28) was tested, in six experiments. Europium release was measured, as determined supra, and the percent of target cells lysed was determined. The results follow:

|  | % LYSIS | |
|---|---|---|
|  | Peptide Added | No Peptide |
| PEPTIDE RLLEFYLAM |  |  |
| Expt 1 | 43 | 0 |
| Expt 2 | 8 | 0 |
| Expt 3 | 9 | 0 |
| PEPTIDE SLAQDAPPL |  |  |
| Expt 1 | 11 | 0 |
| Expt 2 | 13 | 0 |
| Expt 3 | 13 | 0 |
| Expt 4 | 21 | 0 |
| Expt 5 | 12 | 0 |
| Expt 6 | 42 | 0 |

In additional experiments, the CTLs specific to RLLEFY-LAM/HLA-A2 complexes also recognized and lysed melanoma cell line SK-Mel-37 which is known to express both HLA-A2 and NY-ESO-1. This recognition was inhibited via preincubating the target cells with an HLA-A2 binding monoclonal antibody, BB7.2. This confirmed that the CTLs were HLA-A2 specificfor the complexes of the peptide and HLA-A2.

EXAMPLE 24

An additional peptide derived from SSX-4, i.e., STLE-KINKT (SEQ ID NO: 29) was also tested, in the same way the NY-ESO-1 derived peptides were tested. First, ELISPOT assays were carried out, using COS cells which expressed HLA-A*0201, and which either expressed full length SSX-4, due to transfection with cDNA encoding the protein, or which were pulsed with the peptide. Three cultures were tested, in two experiments. The results follow:

|  |  | Pulsed With Peptide | Endogenous NY-ESO-1 Production |
|---|---|---|---|
| Culture 1 | Expt 1 | 50 | 100 |
|  | Expt 2 | 20 | 138 |
| Culture 2 | Expt 1 | 8 | 12 |
|  | Expt 2 | 6 | 14 |
| Culture 3 | Expt 1 | 15 | 47 |
|  | Expt 2 | 14 | 54 |

Further, as with the NY-ESO-1 peptides, specificity of the CTLs was confirmed, using the same assay as described supra, i.e., combining the CTLs generated against the complexes with COS cells, transfected with HLA-A*0201, and pulsed with peptide. The europium release assay described supra was used. The results follow:

|  | % LYSIS | |
|---|---|---|
|  | Peptide Added | No Peptide |
| Expt 1 | 22 | 0 |
| Expt 2 | 14 | 0 |
| Expt 3 | 46 | 0 |
| Expt 4 | 16 | 0 |

As with the NY-ESO-1 derived peptides, CTL recognition was inhibited via preincubation with the monoclonal antibody BB7.2, confirming specificity of the CTL for complexes HLA-A2 and peptides.

EXAMPLE 25

Additional experiments were carried out on peptides derived from SSX-2 i.e, KASEKIFYV (SEQ ID NO: 30), and peptides derived from NY-ESO-1, i.e., SLLMWITQCFL, SLLMWITQC, and QLSLLMWIT (SEQ ID NO: 4-6). In each case, the same type of assays as were carried out in examples 8-11 were carried out. The results were comparable, in that for each peptide, CTL were generated which were specific for the respective peptide/HLA-A2 complex.

EXAMPLE 26

HLA-DR molecules constitute more than 90% of the Class II molecules presented on the surfaces of antigen presenting cells. Hence, there is interest in determining peptides which bind to HLA-DR molecules. Further, there is interest in identifying so-called "promiscuous" peptides which bind to subsets of these molecules, as well as peptides which are specific for only one particular HLA-DR molecule.

Hammer, et al., J. Exp. Med. 180:2353-2358, the discussion of which is incorporated by reference, presents a methodology for determining such peptides. This procedure is also described at www.tepitope.com, and in Hammer et al., "Techniques To Identify The Rules Governing Class II MHC-Peptide Interaction," in Fernandez et al., ed., "MHC Volume 2 A Practical Approach," Oxford University Press, 1998, pages 197-219, incorporated by reference. Further, in a paper by Sturniolo, et al., Nature Biotechnology 17: 555-567 (1999), the disclosure of which is incorporated by reference, a method is described for generating peptide sequences which might bind to particular HLA-Class II molecules. These methodologies were used in connection with the amino acid sequence of NY-ESO-1, set forth supra, and with HLA-DR molecules. These peptides were then synthesized, using standard methods.

The peptides were then combined with autologous dendritic cells. These were obtained by isolating peripheral blood mononuclear cells ("PBMCs" hereafter), from HLA-DR+ donors, using Ficoll-Hypaque methods. These PBMCs were then incubated for 1-2 hours at 37° C., on plastic surfaces. Adherent monocytes were then cultured for 5 days in medium that had been supplemented with IL-4 and GM-CSF. To elaborate, AIMV medium supplemented with 1000 U/ml of IL-4, and 1000 U/ml of GM-CSF was used. This incubation stimulates differentiation into dendritic cells.

Samples of dendritic cells (8×10⁵) were then loaded with 50 μg/ml of endogenously added peptide. The loading proceeded for 2 hours, at 37° C., in medium supplemented with 1000 U/ml of TNF-∝ and 10,000 U/ml of IL-1β. Peptide pulsed dendritic cells were then washed twice, in excess peptide free medium. Then, autologous peripheral blood lymphocytes (4×10⁷) were combined with 8×10⁵ peptide loaded dendritic cells (ratio of 50:1), in medium which contained 5 ng/ml of IL-7 and 20 U/ml of IL-2. Incubation was carried out at 37° C.

Cultures were restimulated weekly with peptide loaded, irradiated PBMCs.

The ability of the peptides to form complexes with HLA-DR molecules and to stimulate CD4+ cell proliferation was determined by measuring BrdU uptake.

The specificity of the resulting CD4+ cells was then tested by combing them with autologous dendritic cells that had been loaded with peptide, admixed with full length recombinant NY-ESO-1 protein, or with an unrelated protein.

The peptides

```
Ser Arg Leu Leu Glu Phe Tyr Leu Ala Met Pro Phe Ala Thr    (SEQ. ID. NO: 31)

and

Phe Leu Pro Val Phe Leu Ala Gln Pro Pro Ser Gly Gln Arg Arg (SEQ. ID. NO: 32)
``` were used.

The peptides were both found to sensitize and to expand CD4+ cells, from two different healthy donors.

EXAMPLE 27

The same protocol referred to supra was then used to determine peptide sequences from SSX-2 which might bind to HLA-DR molecules. The following peptides were identified, and synthesized, using standard methods.

```
Lys Leu Gly Phe Lys Ala Thr Leu Pro Pro Phe Met Cys Asn Lys;  (SEQ. ID. NO: 33)

Gln Met Thr Phe Gly Arg Leu Gln Gly Ile Ser Pro Lys Ile Met;  (SEQ. ID. NO: 34)

Arg Lys Gln Leu Val Ile Tyr Glu Glu Ile Ser Asp Pro Glu Glu   (SEQ. ID. NO: 35)

Lys Ile Phe Tyr Val Tyr Met Lys Arg Lys Tyr Glu Ala Met Thr   (SEQ. ID. NO: 36)

and

Phe Gly Arg Leu Gln Gly Ile Ser Pro Lys Ile Met Pro Lys Lys   (SEQ. ID. NO: 37)
```

These peptides were then tested in competitive binding assays using purified HLA-DR molecules.

The assay is described by Falcioni, et ai., Nature Biotechnoiogy 17: 562-567 (1999), incorporated by reference. In brief, the assay is a "scintiiiation proximity assay" using HLA-DR molecules that had been affinity purified using a monoclonal antibody. The HLA-DR molecules used were DR*0101, DR*1501, DR*0301, DR*1101, DR*0701, and DR*0801. Peptides were tested for their ability to compete with control peptide.

Tyr Ala Phe Arg Ala Ser Ala Lys Ala (SEQ. ID. NO: 38) which Falcioni et al., supra show binds to different HLA-DR molecules. The results are summarized below in terms of the concentration of test peptide (in nm) needed to inhibit binding of control peptide by 50%.

| | HLA-DR Type | | | | | |
|---|---|---|---|---|---|---|
| SEQ. ID. NO: | 0101 | 1501 | 0301 | 1101 | 0701 | 0801 |
| 28 | 0.32 | 0.01 | 3 | 0.5 | 1.6 | 3 |
| 31 | 55 | 4 | 80 | 0.06 | 28 | 0.02 |
| 32 | 36 | 2.1 | 100 | 5 | 1.2 | 30 |

EXAMPLE 28

The results presented supra led to additional experiments using T cells that had been isolated from two donors in the manner described supra. In these experiments, autologous dendritic cells were prepared, as described, and combined with T cells whose proliferation was determined in a BrdU assay. In a first set of experiments, the 5 peptides set forth in example 27 were mixed, and the mixture was compared to an equal amount of full length SSX-2 protein, and an irrelevant protein, "TALL." TALL did not stimulate proliferation at all. The SSX-2 full length molecule provoked just slightly less than 60% proliferation, while the peptide mixture provoked about 85% proliferation.

Similarly, the two peptides of example 1 were mixed, and compared to full length NY-ESO-1 protein, the "TALL" molecule, and unloaded dendritic cells. The mixture provoked just under 20% proliferation, and NY-ESO-1 just under 40%. The other two test samples did not provoke proliferation.

Also, the fact that CD4+ cells proliferate upon contact to cells that had been pulsed with NY-ESO-1 derived peptides and cells pulsed wtih the full length protein indicates that the peptides are produced endogenously by cellular processes, i.e., that the full length molecule (NY-ESO-1) is processed to the relevant peptides of SEQ ID NO: 26 and 27. The pattern of recognition is specific, in that when dendritic cells were mixed with TALL, there was no recognition, nor was there recognition of unpulsed dendritic cells.

The mixture of the two peptides was then compared to each peptide used alone, and to no peptide. In these experiments, the mixture stimulated over 70% proliferation while the individual peptides stimulated about 40%. No proliferation was observed with no peptide. The T cell donor in these experiments had not been typed for HLA-DR molecules.

In a second set of experiments, cells taken from a donor who had been typed as positive for HLA-DR*0101 and HLA-DR*1301 were tested with the individual peptides of example 27, a mix of the peptides, the full length SSX-2 molecule, and the Tall protein described supra. The peptide of SEQ. ID. NO: 33 provoked more proliferation than the other individual peptides or mixture of these, and performed equally as well as the full length molecule.

Six individual experiments were carried out, and in all cases, there was consistently greater T cell proliferation induced by dendritic cells that had been pulsed with SEQ ID NO: 33 or full length SSX-2 than with any of the other peptides, or the TALL molecule. This indicates that the full length molecule is processed to at least one Class II molecule, and that the peptide of SEQ ID NO: 33 can provoke specific $CD4^+$ cells.

The foregoing examples show, inter alia, that tumor rejection antigen precursors, such as NY-ESO-1, SSX-2, and any such molecule identified via the SEREX methodology, is processed to peptides which are presented by MHC-Class I molecules and MHC-Class II molecules as well. Peptides which bind to Class II molecules to form complexes therewith can be used to stimulate proliferation of CD4+ cells. Further, as was shown herein, molecules which contain such sequences can be used to provoke the CD4+ cells as well. The preceding examples show various ways one of ordinary skill in the art can identify molecules which bind to Class II molecules. These should not be taken as the only methodologies by which such molecules could be identified. The skilled artisan will be aware of other approaches to this issue.

A further aspect of the invention is a therapeutic method, wherein one or more peptides which bind to an MHC-Class II molecule on the surface of a patient's tumor cells are administered to the patient, in an amount sufficient for the peptides to bind to the MHC molecules, and provoke lysis by T cells. The exemplification given supra for HLA-DR molecules is by no means the only type of this administration that can be used. Any combination of peptides may be used, such as those for other Class II molecules. These peptides, which may be used alone or in combination, as well as the entire protein or immunoreactive portions thereof, may be administered to a subject in need thereof, using any of the standard types of administration, such as intravenous, intradermal, subcutaneous, oral, rectal, and transdermal administration. Standard pharmaceutical carriers, adjuvants, such as saponins, GM-CSF, and interleukins and so forth may also be used. Further, these peptides and proteins may be formulated into vaccines with the listed material, as may dendritic cells, or other cells which present relevant MHC/peptide complexes. These peptides may also be used to form multimeric complexes of HLA/peptides, such as those described by Dunbar, et al., Curr. Biol. 8: 413-416 (1998), incorporated by reference, wherein four peptide/MHC/biotin complexes are attached to a streptavidin or avidin molecule. Such complexes can be used to identify and/or to stimulate T cell precursors.

Similarly, the invention contemplates therapies wherein the nucleic acid molecule which encodes either full length protein, or one or more of the relevant peptides, in polytope form, is incorporated into a vector, such as an adenovirus based vector, to render it transfectable into eukaryotic cells, such as human cells.

Assays developed from the results presented supra can also be used in progression/regression studies. One can monitor the course of abnormality involving expression of proteins such as NY-ESO-1 or SSX-2, simply by monitoring levels of the protein, its expression, and so forth using any or all of the methods set forth supra, such as identifying CD4+ cell presence and/or levels, using antibodies, peptides, etc.

It should be clear that these methodologies may also be used to track the efficacy of a therapeutic regime. Essentially, one can take a baseline value for the protein, using any of the assays discussed supra, administer a given therapeutic agent, and then monitor levels of the protein thereafter, observing changes in protein levels as indicia of the efficacy of the regime.

As was indicated supra, the invention involves, inter alia, the recognition of an "integrated" immune response to the molecules of interest. One ramification of this is the ability to monitor the course of cancer therapy. In this method, which is a part of the invention, a subject in need of the therapy receives a vaccination of a type described herein. Such a vaccination results, e.g., in a T cell response against cells presenting MHC/peptide complexes on their cells. The response also includes an antibody response, possibly a result of the release of antibody provoking proteins via the lysis of cells by the T cells. Hence, one can monitor the effect of a vaccine, by monitoring an immune response. As is indicated, supra, an increase in antibody titer or T cell count may be taken as an indicia of progress with a vaccine, and vice versa. Hence, a further aspect of the invention is a method for monitoring efficacy of a vaccine, following administration thereof, by determining levels of antibodies in the subject which are specific for the vaccine itself, or a large molecules of which the vaccine is a part.

The effects of a vaccine can also be measured by monitoring the T cell-response of the subject receiving the vaccine. A number of assays can be used to measure the precursor frequency of these in vitro stimulated T cells. These include, but are not limited to, chromium release assays, TNF release assays, $IFN_\gamma$ release assays, an ELISPOT assay, and so forth. Changes in precursor T cell frequencies can be measured and correlated to the efficacy of the vaccine. Additional methods which can be employed include the use of multimeric complexes of MHC/peptides. An example of such complexes is the tetrameric HLA/peptide-biotin-streptavidin system of Dunbar, et al. Curr. Biol. 8: 413-416 (1998), incorporated by reference.

The identification of the subject proteins as being implicated in pathological conditions such as cancer also suggests a number of therapeutic approaches in addition to those discussed supra. The experiments set forth supra establish that antibodies are produced in response to expression of the protein. Hence, a further embodiment of the invention is the treatment of conditions which are characterized by aberrant or abnormal levels of the proteins, via administration of antibodies, such as humanized antibodies, antibody fragments, and so forth. These may be tagged or labelled with appropriate cystostatic or cytotoxic reagents.

T cells may also be administered. It is to be noted that the T cells may be elicited in vitro using immune responsive cells such as dendritic cells, lymphocytes, or any other immune responsive cells, and then reperfused into the subject being treated.

Note that the generation of T cells and/or antibodies can also be accomplished by administering cells, preferably treated to be rendered non-proliferative, which present relevant T cell or B cell epitopes for response, such as the epitopes discussed supra.

The therapeutic approaches may also include antisense therapies, wherein an antisense molecule, preferably from 10 to 100 nucleotides in length, is administered to the subject either "neat" or in a carrier, such as a liposome, to facilitate incorporation into a cell, followed by inhibition of expression of the protein. Such antisense sequences may also be incorporated into appropriate vaccines, such as in viral vectors (e.g., Vaccinia), bacterial constructs, such as variants of the known BCG vaccine, and so forth.

CD4+ cells respond to complexes of MHC-Class II molecules and peptides, and MHC-Class II restricted CD4+ T cell responses against recombinant NY-ESO-1, presented by autologous cultured dendritic cells have been detected in melanoma patients. Specifically, CD4+ cells were separated from other cells from PBLs or serum samples, using well known techniques. Then, they were admixed with dendritic cells which had been pulsed with NY-ESO-1 protein. Proliferation of CD4+ cells was observed, bringing another facet to the integrated immune response discussed herein. Hence, a further aspect of this invention are these CD4+ T cells, peptides which bind to the MHC-Class II molecules, and their use in therapy.

As the examples indicate, ESO-1 is also processed to peptides which complex to MHC Class II molecules, HLA-DR53 in particular.

Other features and applications of the invention will be clear to the skilled artisan, and need not be set forth herein.

The terms and expression which have been employed are used as terms of description and not of limitation, and there is no intention in the use of such terms and expression of excluding any equivalents of the features shown and described or portions thereof, it being recognized that various modifications are possible within the scope of the invention.

We claim:

1. An isolated nucleic acid molecule consisting of a nucleotide sequence which encodes the isolated polypeptide of SEQ ID NO: 32, 33, 34, 35, 36 or 37.

2. The isolated nucleic acid molecule of claim 1 consisting of a nucleotide sequence which encodes the isolated polypeptide of SEQ ID NO: 32.

3. The isolated nucleic acid molecule of claim 1 consisting of a nucleotide sequence which encodes the isolated polypeptide of SEQ ID NO: 33.

4. The isolated nucleic acid molecule of claim 1 consisting of a nucleotide sequence which encodes the isolated polypeptide of SEQ ID NO: 34.

5. The isolated nucleic acid molecule of claim 1 consisting of a nucleotide sequence which encodes the isolated polypeptide of SEQ ID NO: 35.

6. The isolated nucleic acid molecule of claim 1 consisting of a nucleotide sequence which encodes the isolated polypeptide of SEQ ID NO: 36.

7. The isolated nucleic acid molecule of claim 1 consisting of a nucleotide sequence which encodes the isolated polypeptide of SEQ ID NO: 37.

8. A recombinant cell comprising the isolated nucleic acid molecule of claim 1.

9. An expression vector comprising the isolated nucleic acid molecule of claim 1, operably linked to a promoter.

10. A recombinant cell comprising the expression vector of claim 8.

11. An isolated nucleic acid molecule consisting of a nucleotide sequence which encodes an isolated polypeptide which binds to at least one MHC Class II, HLA-DR molecule, selected from the group consisting of HLA-DR*0101, HLA-DR*1501, HLA-DR*0301, HLA-DR*1101, HLA-DR*0701, and HLA-DR*0801, wherein said, isolated polypeptide consists of from 14 to 25 contiguous amino acids found within the tumor rejection antigen precursor NY-ESO-1, which is encoded by the nucleotide sequence set forth in SEQ ID NO: 1.

12. A recombinant cell comprising the isolated nucleic acid molecule of claim 11.

13. An expression vector comprising the isolated nucleic acid molecule of claim 11, operably linked to a promoter.

14. A recombinant, cell comprising the expression vector of claim 13.

15. An expression kit comprising a separate portion of each of (i) an isolated nucleic acid molecule which encodes the isolated peptide of SEQ ID NO; 32, 33, 34, 35, 36 or 37, and (ii) an isolated nucleic acid molecule which encodes an HLA-DR molecule, selected from the group consisting of HLA-DR*0101, HLA-DR*1501, HLA-DR*0301, HLA-DR*1101, HLA-DR*0701, and HLA-DR*0801, wherein said HLA-DR molecule forms a complex with said peptide of (i).

* * * * *

SEQUENCE LISTING

<160> NUMBER OF SEQ ID NOS: 38

<210> SEQ ID NO 1
<211> LENGTH: 752
<212> TYPE: DNA
<213> ORGANISM: Homo sapiens
<220> FEATURE:

<400> SEQUENCE: 1

```
atcctcgtgg gccctgacct tctctctgag agccgggcag aggctccgga gccatgcagg      60
ccgaaggccg gggcacaggg ggttcgacgg gcgatgctga tggcccagga ggccctggca     120
ttcctgatgg cccaggggc  aatgctggcg gcccaggaga ggcgggtgcc acgggcggca     180
gaggtccccg gggcgcaggg gcagcaaggg cctcggggcc gggaggaggc gccccgcggg     240
gtccgcatgg cggcgcggct tcagggctga atggatgctg cagatgcggg gccagggggc     300
cggagagccg cctgcttgag ttctacctcg ccatgccttt cgcgacaccc atggaagcag     360
agctggcccg caggagcctg gcccaggatg ccccaccgct tcccgtgcca ggggtgcttc     420
tgaaggagtt cactgtgtcc ggcaacatac tgactatccg actgactgct gcagaccacc     480
gccaactgca gctctccatc agctcctgtc tccagcagct ttccctgttg atgtggatca     540
cgcagtgctt tctgcccgtg ttttggctc  agcctccctc agggcagagg cgctaagccc     600
agcctggcgc cccttcctag gtcatgcctc ctccccctagg gaatggtccc agcacgagtg     660
gccagttcat tgtgggggcc tgattgtttg tcgctggagg aggacggctt acatgtttgt     720
ttctgtagaa aataaaactg agctacgaaa aa                                   752
```

<210> SEQ ID NO 2
<211> LENGTH: 31
<212> TYPE: DNA
<213> ORGANISM: Homo sapiens
<220> FEATURE:

<400> SEQUENCE: 2

```
cacacaggat ccatggatgc tgcagatgcg g                                     31
```

<210> SEQ ID NO 3
<211> LENGTH: 32
<212> TYPE: DNA
<213> ORGANISM: Homo sapiens

-continued

```
<220> FEATURE:

<400> SEQUENCE: 3
cacacaaagc ttggcttagc gcctctgccc tg                                     32

<210> SEQ ID NO 4
<211> LENGTH: 11
<212> TYPE: PRT
<213> ORGANISM: Homo sapiens

<400> SEQUENCE: 4

Ser Leu Leu Met Trp Ile Thr Gln Cys Phe Leu
1               5                   10

<210> SEQ ID NO 5
<211> LENGTH: 9
<212> TYPE: PRT
<213> ORGANISM: Homo sapiens

<400> SEQUENCE: 5

Ser Leu Leu Met Trp Ile Thr Gln Cys
1               5

<210> SEQ ID NO 6
<211> LENGTH: 9
<212> TYPE: PRT
<213> ORGANISM: Homo sapiens

<400> SEQUENCE: 6

Gln Leu Ser Thr Leu Met Trp Ile Thr
1               5

<210> SEQ ID NO 7
<211> LENGTH: 18
<212> TYPE: PRT
<213> ORGANISM: Homo sapiens

<400> SEQUENCE: 7

Ala Ala Asp His Arg Gln Leu Gln Leu Ser Ile Ser Ser Cys Leu Gln
1               5                   10                  15

Gln Leu

<210> SEQ ID NO 8
<211> LENGTH: 18
<212> TYPE: PRT
<213> ORGANISM: Homo sapiens

<400> SEQUENCE: 8

Val Leu Leu Lys Glu Phe Thr Val Ser Gly Asn Ile Leu Thr Ile Arg
1               5                   10                  15

Leu Thr

<210> SEQ ID NO 9
<211> LENGTH: 18
<212> TYPE: PRT
<213> ORGANISM: Homo sapiens

<400> SEQUENCE: 9

Pro Leu Pro Val Pro Gly Val Leu Leu Lys Glu Phe Thr Val Ser Gly
1               5                   10                  15

Asn Ile
```

```
<210> SEQ ID NO 10
<211> LENGTH: 18
<212> TYPE: PRT
<213> ORGANISM: Homo sapiens

<400> SEQUENCE: 10

Gly Ala Ala Ser Gly Leu Asn Gly Cys Cys Arg Cys Gly Ala Arg Gly
1               5                   10                  15

Pro Glu

<210> SEQ ID NO 11
<211> LENGTH: 18
<212> TYPE: PRT
<213> ORGANISM: Homo sapiens

<400> SEQUENCE: 11

Ser Arg Leu Leu Glu Phe Tyr Leu Ala Met Pro Phe Ala Thr Pro Met
1               5                   10                  15

Glu Ala

<210> SEQ ID NO 12
<211> LENGTH: 18
<212> TYPE: PRT
<213> ORGANISM: Homo sapiens

<400> SEQUENCE: 12

Thr Val Ser Gly Asn Ile Leu Thr Ile Arg Leu Thr Ala Ala Asp His
1               5                   10                  15

Arg Gln

<210> SEQ ID NO 13
<211> LENGTH: 23
<212> TYPE: DNA
<213> ORGANISM: Homo sapiens

<400> SEQUENCE: 13
cacacaggat ccatgaacgg aga                                          23

<210> SEQ ID NO 14
<211> LENGTH: 33
<212> TYPE: DNA
<213> ORGANISM: Homo sapiens

<400> SEQUENCE: 14
cacacaaagc tttgagggga gttactcgtc atc                               33

<210> SEQ ID NO 15
<211> LENGTH: 23
<212> TYPE: DNA
<213> ORGANISM: Homo sapiens

<400> SEQUENCE: 15
ctaaagcatc agagaagaga agc                                          23

<210> SEQ ID NO 16
<211> LENGTH: 26
<212> TYPE: DNA
<213> ORGANISM: Homo sapiens

<400> SEQUENCE: 16
agatctctta ttaatcttct cagaaa                                       26
```

```
<210> SEQ ID NO 17
<211> LENGTH: 23
<212> TYPE: DNA
<213> ORGANISM: Homo sapiens

<400> SEQUENCE: 17
gtgctcaaat accagagaag atc                                            23

<210> SEQ ID NO 18
<211> LENGTH: 22
<212> TYPE: DNA
<213> ORGANISM: Homo sapiens

<400> SEQUENCE: 18
ttttgggtcc agatctctcg tg                                             22

<210> SEQ ID NO 19
<211> LENGTH: 24
<212> TYPE: DNA
<213> ORGANISM: Homo sapiens

<400> SEQUENCE: 19
ggaagagtgg gaaaagatga aagt                                           24

<210> SEQ ID NO 20
<211> LENGTH: 22
<212> TYPE: DNA
<213> ORGANISM: Homo sapiens

<400> SEQUENCE: 20 cccctttttgg gtccagatat ca                                            22

<210> SEQ ID NO 21
<211> LENGTH: 25
<212> TYPE: DNA
<213> ORGANISM: Homo sapiens

<400> SEQUENCE: 21
aaatcgtcta tgtgtatatg aagct                                          25

<210> SEQ ID NO 22
<211> LENGTH: 23
<212> TYPE: DNA
<213> ORGANISM: Homo sapiens

<400> SEQUENCE: 22
gggtcgctga tctcttcata aac                                            23

<210> SEQ ID NO 23
<211> LENGTH: 23
<212> TYPE: DNA
<213> ORGANISM: Homo sapiens

<400> SEQUENCE: 23
gttctcaaat accacagaag atg                                            23

<210> SEQ ID NO 24
<211> LENGTH: 21
<212> TYPE: DNA
<213> ORGANISM: Homo sapiens

<400> SEQUENCE: 24
ctctgctggc ttctcgggcc g                                              21
```

-continued

```
<210> SEQ ID NO 25
<211> LENGTH: 27
<212> TYPE: DNA
<213> ORGANISM: Homo sapiens

<400> SEQUENCE: 25
acagcattac caaggacagc agccacc                                              27

<210> SEQ ID NO 26
<211> LENGTH: 27
<212> TYPE: DNA
<213> ORGANISM: Homo sapiens

<400> SEQUENCE: 26
gccaacagca agatgcatac cagggac                                              27

<210> SEQ ID NO 27
<211> LENGTH: 9
<212> TYPE: PRT
<213> ORGANISM: Homo sapiens

<400> SEQUENCE: 27

Arg Leu Leu Glu Phe Tyr Leu Ala Met
1               5

<210> SEQ ID NO 28
<211> LENGTH: 9
<212> TYPE: PRT
<213> ORGANISM: Homo sapiens

<400> SEQUENCE: 28

Ser Leu Ala Gln Asp Ala Pro Pro Leu
1               5

<210> SEQ ID NO 29
<211> LENGTH: 9
<212> TYPE: PRT
<213> ORGANISM: Homo sapiens

<400> SEQUENCE: 29

Ser Thr Leu Glu Lys Ile Asn Lys Thr
1               5

<210> SEQ ID NO 30
<211> LENGTH: 9
<212> TYPE: PRT
<213> ORGANISM: Homo sapiens

<400> SEQUENCE: 30

Lys Ala Ser Glu Lys Ile Phe Tyr Val
1               5

<210> SEQ ID NO 31
<211> LENGTH: 14
<212> TYPE: PRT
<213> ORGANISM: Homo sapiens

<400> SEQUENCE: 31

Ser Arg Leu Leu Glu Phe Tyr Leu Ala Met Pro Phe Ala Thr
1               5                   10

<210> SEQ ID NO 32
<211> LENGTH: 15
<212> TYPE: PRT
```

<213> ORGANISM: Homo sapiens

<400> SEQUENCE: 32

Phe Leu Pro Val Phe Leu Ala Gln Pro Pro Ser Gly Gln Arg Arg
1               5                   10                  15

<210> SEQ ID NO 33
<211> LENGTH: 15
<212> TYPE: PRT
<213> ORGANISM: Homo sapiens

<400> SEQUENCE: 33

Lys Leu Gly Phe Lys Ala Thr Leu Pro Pro Phe Met Cys Asn Lys
1               5                   10                  15

<210> SEQ ID NO 34
<211> LENGTH: 15
<212> TYPE: PRT
<213> ORGANISM: Homo sapiens

<400> SEQUENCE: 34

Gln Met Thr Phe Gly Arg Leu Gln Gly Ile Ser Pro Lys Ile Met
1               5                   10                  15

<210> SEQ ID NO 35
<211> LENGTH: 15
<212> TYPE: PRT
<213> ORGANISM: Homo sapiens

<400> SEQUENCE: 35

Arg Lys Gln Leu Val Ile Tyr Glu Glu Ile Ser Asp Pro Glu Glu
1               5                   10                  15

<210> SEQ ID NO 36
<211> LENGTH: 15
<212> TYPE: PRT
<213> ORGANISM: Homo sapiens

<400> SEQUENCE: 36

Lys Ile Phe Tyr Val Tyr Met Lys Arg Lys Tyr Glu Ala Met Thr
1               5                   10                  15

<210> SEQ ID NO 37
<211> LENGTH: 15
<212> TYPE: PRT
<213> ORGANISM: Homo sapiens

<400> SEQUENCE: 37

Phe Gly Arg Leu Gln Gly Ile Ser Pro Lys Ile Met Pro Lys Lys
1               5                   10                  15

<210> SEQ ID NO 38
<211> LENGTH: 9
<212> TYPE: PRT
<213> ORGANISM: Homo sapiens

<400> SEQUENCE: 38

Tyr Ala Phe Arg Ala Ser Ala Lys Ala
1               5